(12) United States Patent
Thomas

(10) Patent No.: US 7,977,053 B2
(45) Date of Patent: Jul. 12, 2011

(54) CIRCULAR PROBE AMPLIFICATION (CPA) USING ENERGY-TRANSFER PRIMERS

(75) Inventor: David C. Thomas, Germantown, MD (US)

(73) Assignee: Virco BVBA, Mechelen (BE)

( * ) Notice: Subject to any disclaimer, the term of this patent is extended or adjusted under 35 U.S.C. 154(b) by 100 days.

(21) Appl. No.: 11/609,436

(22) Filed: Dec. 12, 2006

(65) Prior Publication Data
US 2007/0218477 A1 Sep. 20, 2007

Related U.S. Application Data

(63) Continuation of application No. 10/469,099, filed as application No. PCT/EP02/02287 on Feb. 27, 2002, now abandoned.

(60) Provisional application No. 60/271,433, filed on Feb. 27, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......... 435/6; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 4,518,584 A | 5/1985 | Mark et al. | |
| 4,683,195 A | 7/1987 | Mullis et al. | |
| 4,683,202 A | 7/1987 | Mullis | |
| 4,737,462 A | 4/1988 | Mark et al. | |
| 4,925,785 A | 5/1990 | Wang et al. | |
| 4,996,143 A | 2/1991 | Heller et al. | |
| 5,119,801 A | 6/1992 | Eizenhoefer et al. | |
| 5,124,246 A | 6/1992 | Urdea et al. | |
| 5,312,728 A | 5/1994 | Lizardi et al. | |
| 5,348,853 A | 9/1994 | Wang et al. | |
| 5,409,818 A | 4/1995 | Davey et al. | |
| 5,438,131 A * | 8/1995 | Bergstrom et al. | .......... 536/28.6 |
| 5,494,810 A | 2/1996 | Barany et al. | |
| 5,532,129 A | 7/1996 | Heller | |
| 5,545,522 A | 8/1996 | Van Gelder et al. | |
| 5,565,322 A | 10/1996 | Heller | |
| 5,593,840 A | 1/1997 | Bhatnagar et al. | |
| 5,714,320 A | 2/1998 | Kool | |

(Continued)

FOREIGN PATENT DOCUMENTS
WO   WO-94006810 A1   3/1994
(Continued)

OTHER PUBLICATIONS

Thomas, D.C. et al., Arch. Pathol. Med., vol. 123, pp. 1170-1176 (1999).*

(Continued)

*Primary Examiner* — Teresa E Strzelecka
(74) *Attorney, Agent, or Firm* — Patton Boggs LLP

(57) ABSTRACT

The present invention provides methods and kits for the rapid exponential amplification of nucleic acid molecules using a padlock probe. The present invention improves upon the existing methods for amplifying padlock probes by eliminating or delaying the appearance of artifact products that cause false positive results, and also increase the sensitivity and speed of the assay. Further provided are nucleic acid amplification primers containing non-informative base analogs.

41 Claims, 5 Drawing Sheets

U.S. PATENT DOCUMENTS

| | | | |
|---|---|---|---|
| 5,854,033 A | 12/1998 | Lizardi | |
| 5,866,336 A | 2/1999 | Nazarenko et al. | |
| 5,912,124 A | 6/1999 | Kumar | |
| 5,916,750 A | 6/1999 | Iyer et al. | |
| 6,007,994 A | 12/1999 | Ward et al. | |
| 6,077,668 A | 6/2000 | Kool | |
| 6,090,552 A | 7/2000 | Nazarenko et al. | |
| 6,096,880 A | 8/2000 | Kool | |
| 6,117,635 A | 9/2000 | Nazarenko et al. | |
| 6,143,495 A * | 11/2000 | Lizardi et al. | 435/6 |
| 6,383,752 B1 | 5/2002 | Agrawal et al. | |
| 6,399,304 B1 * | 6/2002 | Kilger et al. | 435/6 |
| 6,403,319 B1 | 6/2002 | Lizardi et al. | |

FOREIGN PATENT DOCUMENTS

| | | |
|---|---|---|
| WO | WO-00036141 A1 | 6/2000 |
| WO | WO-02068683 A2 | 9/2002 |

OTHER PUBLICATIONS

Metzker, M.L. et al., Nucl. Acids Res., vol. 22, pp. 4259-4267 (1994).*

In the US Patent and Trademark Office U.S. Appl. No. 10/469,099, Non-Final Office Action dated Jun. 12, 2006, 13 pages.

Aliotta et al.; *Thermostable Bst DNA polymerase I lacks a 3'→5' proofreading exonuclease activity*; Genetic Analysis Biomolecular Engineering; 1996; 12(5-6):185-195.

Baner et al.; *Signal amplification of padlock probes by rolling circle replication*; Nucleic Acids Research; 1998; vol. 26, No. 22; pp. 5073-5078.

Bauer et al.; *A genetic enrichment for mutations constructed by oligodeoxynucleotide-directed mutagenesis*; Gene.; 1985; vol. 37; pp. 73-81.

Boehmer et al.; *Herpes Simplex Virus Type 1 ICP8: Helix-Destabilizing Properties*; Journal of Virology; Feb. 1993; vol. 67, No. 2; pp. 711-715.

Craik, Charles S.; *Use of Oligonucleotides for Site-Specific Mutagenesis*; BioTechniques; Jan./Feb. 1985; pp. 12-19.

Devereux et al.; *A comprehensive set of sequence analysis programs for the VAX*; Nucleic Acids Research; 1984; IRL Press Limited, Oxford, England; vol. 12, No. 1; pp. 387-395.

Esteller et al.; *Inactivation of the DNA-Repair Gene MGMT and the Clinical Response of Gliomas to Alkylating Agents*; The New England Journal of Medicine; 2000; vol. 343, No. 19; pp. 1350-1354; correction 1740a; correction 2001; 344:686(3 pages).

Fire et al.; *Rolling replication of short DNA circles*; Proc. Natl. Acad. Sci. (USA); May 1995; vol. 92; pp. 4641-4645.

Graff et al.; *E-Cadherin Expression Is Silenced by DNA Hypermethylation in Human Breast and Prostate Carcinomas*; Cancer Research; 1995; vol. 55; pp. 5195-5199.

Gribskov et al.; *Sigma factors from E. coli, B. subtilis, phage SP01, and phage T4 are homologous proteins*; Nucleic Acids Research; 1986; vol. 14, No. 1; pp. 6745-6763.

Guo et al.; *Direct fluorescence analysis of genetic polymorphisms by hybridization with oligonucleotide arrays on glass supports*; Nucleic Acids Research; 1994; vol. 22, No. 24; pp. 5456-5465.

Hatt et al.; *Analysis of the entire nucleotide sequence of the cryptic plasmid of Chlamydia trachomatis serovar L1. Evidence for involvement in DNA replication*; Nucleic Acids Research; 1988; vol. 16, No. 9; pp. 4053-4067.

Herman et al.; *Hypennethylation-associated Inactivation Indicates a Tumor Suppressor Role for p15$_{INK4B1}$*; Cancer Research; 1996; vol. 56; pp. 722-727.

Herman et al.; *Methylation-specific PCR: A novel PCR assay for methylation status of CpG islands*; Proc. Natl. Acad. Sci. (USA); 1996; vol. 93; pp. 9821-9826.

Herman et al.; *Silencing of the VHL tumor-suppressor gene by DNA methylation in renal carcinoma*; Proc. Natl. Acad. Sci. (USA); 1994; vol. 91; pp. 9700-9704.

Holland et al.; *Detection of specific polymerase chain reaction product by utilizing the 5'→3' exonuclease activity of Thermus aquaticus DNA polymerase*; Proc. Natl. Acad. Sci. (USA); 1991; vol. 88; pp. 7276-7280.

Kaplan et al.; *Rapid Photolytic Release of Adenosine 5'-Triphosphate from a Protected Analogue: Utilization by the Na:K Pump of Human Red Blood Cell Ghosts*; 1978; American Chemical Society; vol. 17, No. 10; pp. 1929-1935.

Khrapko et al.; *Hybridization of DNA with Oligonucleotides Immobilized in Gel: Convenient Method for Detection of Single Base Changes*; Molekuliarnaia Biologiia (USSR); 1991; vol. 25, No. 3; pp. 718-730. (With English Language Abstract).

Kievitis et al.; *NASBA™ isothermal enzymatic in vitro nucleic acid amplification optimized for the diagnosis of HIV-1 infection*; Journal of Virological Methods, 1991; vol. 35; pp. 273-286.

Kunkel et al.; *Rapid and Efficient Site-Specific Mutagenesis without Phenotypic Selection*; Methods in Enzymology; 1987; vol. 154; pp. 367-382.

Kunkel, Thomas A.; *Rapid and efficient site-specific mutagenesis without phenotypic selection*; Proc. Natl. Acad. Sci. (USA); 1985; vol. 82; pp. 488-492.

Kwoh et al.; *Transcription-based amplification system and detection of amplified human immunodeficiency virus type 1 with a bead-based sandwich hybridization format*; Proc. Natl. Acad. Sci. (USA); 1989; vol. 86; pp. 1173-1177.

Landegren et al; *A Ligase-Mediated Gene Detection Technique*; Science; 1988; vol. 241; pp. 1077-1080.

Lee et al.; *Allelic discrimination by nick-translation PCR with fluorogenic probes*; Nucleic Acids Research; 1993; vol. 21, No. 16; pp. 3761-3766.

Lee et al.; *CG Island Methylation Changes Near the GSTP1 Gene in Prostatic Carcinoma Cells Detected Using The Polymerase Chain Reaction: A New Prostate Cancer Biomarker*; Cancer Epidemiology, Biomarkers & Prevention; 1997; vol. 6; pp. 443-450.

Lizardi et al.; *Mutation detection and single-molecule counting using isothermal rolling-circle amplification*; Nature Genetics; 1998; vol. 19; pp. 225-232.

Loakes et al.; *3-Nitropyrrole and 5-nitroindole as universal bases in primers for DNA sequencing and PCR*; Nucleic Acids Research; 1995; vol. 23, No. 13; pp. 2361-2366.

Lu et al.; *Large Fragment of DNA Polymerase I from Bacillus stearothermophilus (Bst Polymerase) is Stable at Ambient Temperature*; BioTechniques; 1991; vol. 11, No. 4; pp. 464, 466.

Luo et al.; *Improving the fidelity of Thermus thermophilus DNA ligase*; Nucleic Acids Research; 1996; vol. 24, No. 14; pp. 3071-3078.

Marras et al.; *Multiplex detection of single-nucleotide variations using molecular beacons*; Genetic Analysis: Biomolecular Engineering; 1999; vol. 14; pp. 151-156.

McCray et al.; *A new approach to time-resolved studies of ATP-requiring biological systems: Laser flash photolysis of caged ATP*; Proc. Natl. Acad. Sci. (USA); 1980; vol. 77, No. 12; pp. 7237-7241.

Merlo et al.; *5' CpG island methylation is associated with transcriptional silencing of the tumour suppressor p16/CDKN2/MTS1 in human cancers*; Nature Medicine; 1995; vol. 1, No. 7; pp. 686-692.

Metzker et al.; *Termination of DNA synthesis by novel 3'-modified-deoxyribonucleosides 5'-triphosphates*; Nucleic Acids Research; 1994; Vol. 22(20); pp. 4259-4267.

Nazarenko et al.; *A closed tube format for amplification and detection of DNA based on energy transfer*, Nucleic Acids Research; 1997; vol. 25, No. 12; pp. 2516-2521.

Needleman et al.; *A General Method Applicable to the Search for Similarities in the Amino Acid Sequence of Two Proteins*; J. Mol. Biol.; 1970; vol. 48; pp. 443-453.

Nilsson et al.; *Padlock Probes: Circularizing Oligonucleotides for Localized DNA Detection*; Science; 1994; vol. 265; pp. 2085-2088.

Nuovo et al.; *In Situ Amplification Using Universal Energy Transfer-labled Primers*; The Journal of Histochemistry & Cytochemistry; 1999; vol. 47, No. 3; pp. 273-279.

Pease et al.; *Light-generated oligonucleotide arrays for rapid DNA sequence analysis*; Proc. Natl. Acad. Sci. (USA); 1994; vol. 91; pp. 5022-5026.

Phang et al.; *Cloning and complete sequence of the DNA polymerase-encoding gene (Bstpoll) and characterisation of the Klenow-like fragment from Bacillus stearothermophilus*; Gene; 1995; vol. 163; pp. 65-68.

Riggs et al.; *Construction of single amino acid substitution mutants of cloned Bacillus stearothermophilus Dna polymerase I which lack 5'→3' exonuclease activity*; Biochimica et Biophysica Acta; 1996; vol. 1307; pp. 178-186.

Rigler et al.; *Differences in the Mechanism of Stimulation of T7 DNA Polymerase by Two Binding Modes of Escherichia coli Single-stranded DNA-binding Protein*; The Journal of Biological Chemistry; 1995; vol. 270, No. 15; pp. 8910-8919.

Saiki et al.; *Enzymatic Amplification of βGlobin Genomic Sequences and Restriction Site Analysis for Diagnosis of Sickle Cell Anemia*; Science; 1985; vol. 230; pp. 1350-1354.

Schwartz et al.; *Matrices for Detecting Distant Relationships*; Atlas of Protein Sequence and Structure; 1978; vol. 5, Supplement 3; pp. 353-358.

Siegal et al.; *A Novel DNA Helicase from Calf Thymus*; The Journal of Biological Chemistry; 1992; vol. 267, No. 19; pp. 13629-13635.

Skaliter et al.; *Rolling circle DNA replication in vitro by a complex of heroes simplex virus type 1-encoded enzymes*; Proc. Natl. Acad. Sci. (USA); 1994; vol. 91; pp. 10665-10669.

Smith et al.; *Comparison of Biosequences*; Advances in Applied Mathematics; 1981; vol. 2; pp. 482-489.

Thomas et al.; *Amplification of Padlock Probes for DNA Diagnostics by Cascade Rolling Circle Amplification or the Polymerase Chain Reaction*; Archives of Pathology and Laboratory Medicine; Dec. 1999; vol. 123, No. 12; pp. 1170-1176.

Tsurumi et al.; *Functional Interaction between Epstein-Barr Virus DNA Polymerase Catalytic Subunit and Its Accessory Subunit In Vitro*; Journal of Virology; 1993; vol. 67, No. 12; pp. 7648-7653.

Tyagi et al.; *Molecular Beacons: Probes that Fluoresce upon Hybridization*; Nature Biotechnology; 1996; vol. 14; pp. 303-308.

Uehara et al.; *Detection of Telomerase Activity Utilizing Energy Transfer Primers: Comparison with Gel- and Elisa-Based Detection*; BioTechniques; 1999; vol. 26; pp. 552558.

Walder et al.; *Oligodeoxynucleotide-directed mutagenesis using the yeast transformation system*; Gene; 1986; vol. 42; pp. 133-139.

Walker et al.; *Isothermal in vitro amplification of DNA by a restriction enzyme/DNA polymerase system*; Proc. Natl. Acad. Sci. (USA); 1992; vol. 89; pp. 392-396.

Walker et al.; *Strand displacement amplification - an isothermal, in vitro DNA amplification technique*; Nucleic Acids Research; 1992; vol. 20, No. 7; pp. 1691-1696.

Wang et al.; *Rapid Sizing of Short Tandem Repeat Alleles Using Capillary Array Electrophoresis and Energy-Transfer Fluorescent Primers*; Analytical Chemistry; 1995; vol. 67, No. 7; pp. 1197-1203.

Zhang et al.; *Amplification of target-specific, ligation-dependent circular probe*; Gene; 1998; vol. 211; pp. 277-285.

Zijderveld et al.; *Helix-Destabilizing Properties of the Adenovirus DNA-Binding Protein*; Journal of Virology; 1994; vol. 68, No. 2; pp. 1158-1164.

\* cited by examiner

Circular Probe Amplification

A. Rolling circle amplifcation using forward primer, bind reverse primer

B. Cascade rolling circle amplifcation with two primers

C. Polymerase chain reaction of cascade products

Amplification of padlock probes by PCR or CPA
FIGURE 4A
PCR
(Deep Vent)
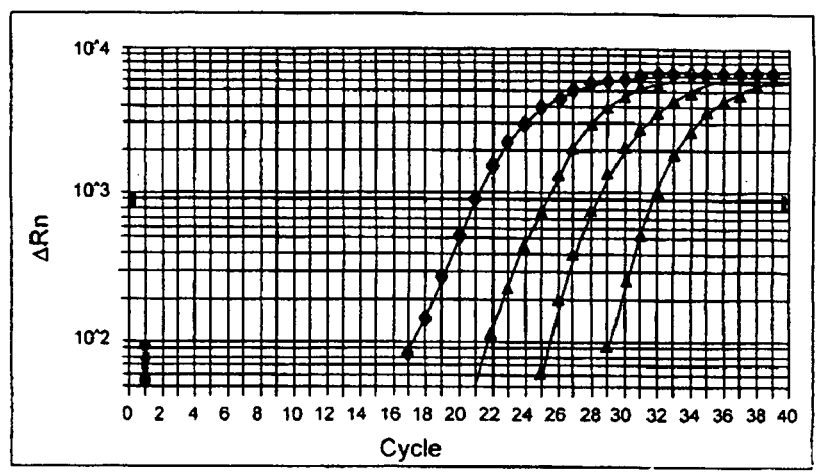
CPA
(Deep Vent
+ Bst LF)
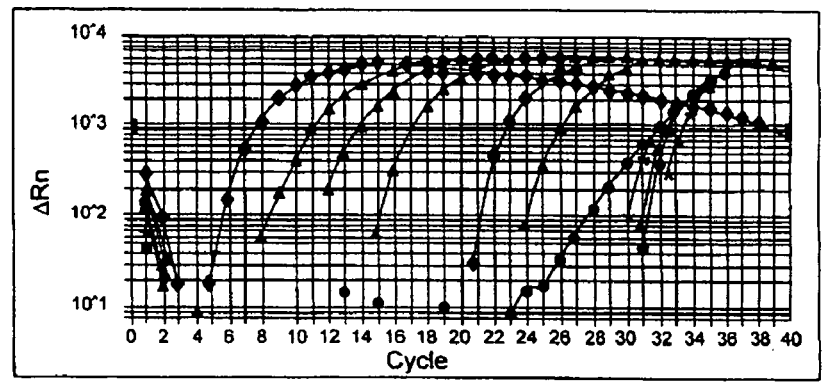
FIGURE 4B Amplification of padlock probes by PCR or CPA
FIGURE 5A
PCR
(Plat. Taq)
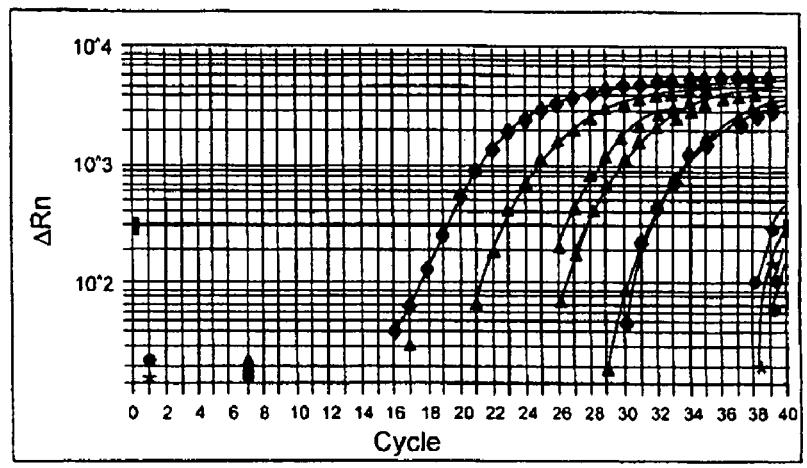
CPA
(Plat. Taq +
Bst LF)
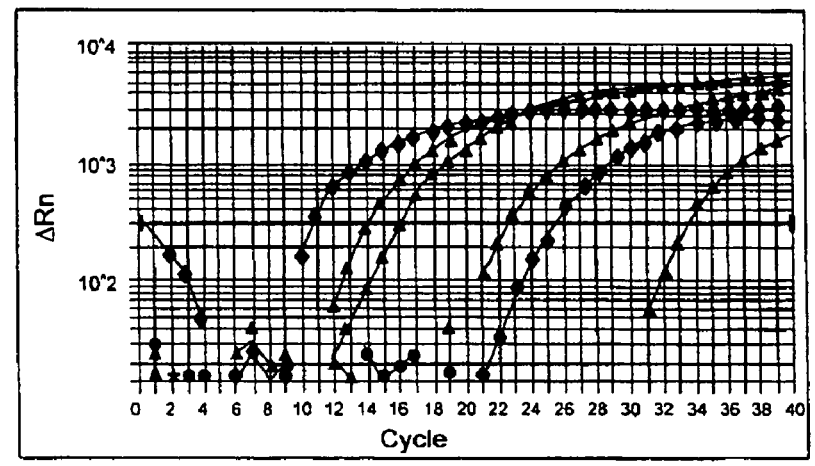
FIGURE 5 B

CIRCULAR PROBE AMPLIFICATION (CPA) USING ENERGY-TRANSFER PRIMERS

CROSS REFERENCE TO RELATED APPLICATIONS

This Application is a Continuation application of U.S. application Ser. No. 10/469,099 filed Aug. 22, 2003, now abandoned which Application is a 35 U.S.C. §371 national phase application of PCT/EP02/02287, with an international filing date of Feb. 27, 2002, which claims priority to U.S. application Ser. No. 60/271,433, filed on Feb. 27, 2001, the complete disclosures of which are hereby incorporated by reference in their entirety.

STATEMENT OF GOVERNMENT RIGHTS

The present invention was supported, in part, by Small Business Innovation grants from the National Institute of Allergy and Infectious Diseases (1R43AI42481-01 and 5R44AI42481-03). The Government has certain rights in the invention.

FIELD OF THE INVENTION

The present invention relates to methods and reagents for the exponential amplification of circularized nucleic acid molecules. The present invention further relates to methods and reagents for detecting and amplifying specific nucleic acid molecules from a sample.

There are several reported methods for amplifying nucleic acids. These methods fall into one of two categories, isothermal or thermal cycling techniques. PCR is generally considered the most common thermal cycling technique. Saiki et al., Science 230:1350-1354 (1985), U.S. Pat. Nos. 4,683,195 and 4,683,202, all of which are herein incorporated by reference. Other thermal cycling techniques for amplifying nucleic acid molecules include the ligase chain reaction (LCR) Landegren et al., Science 241:1077-1080 (1988), herein incorporated by reference).

Isothermal reactions, as the name implies, are run at a uniform temperature, usually higher than room temperature to improve fidelity. Some of the reported isothermal methods include strand displacement reaction (SDA) (Walker et al., Proc. Nat'l Acad. Sci. (USA) 89:32-396 (1992); Walker et al., Nucleic Acids Res. 20:1691-1696 (1992), both of which are herein incorporated by reference), nucleic acid based amplification (NASBA) (Kievitis et al., J. Virol. Methods 35:273-286 (1991), and U.S. Pat. No. 5,409,818, both of which are herein incorporated by reference), and transcription mediated amplification (TMA) (Kwoh et al., Proc. Natl. Acad. Sci. (U.S.A.) 86:1173-1177 (1989), herein incorporated by reference).

The rolling circle amplification (RCA) method is another isothermal reaction. Various forms of RCA have been reported. Lizardi et al., Nature Genetics 19:225-232 (1998) and Zhang et al., Gene 211:277-85 (1998), both of which are herein incorporated by reference. This technique is the linear amplification of a circular DNA probe, commonly referred to as a "padlock probe." Another isothermal nucleic acid amplification method employing padlock probes is the exponential rolling circle amplification method, Cascade Rolling Circle Amplification (CRCA) method.

Padlock probes were first introduced in 1994 and methods have been developed for utilizing these probes in molecular diagnostics, both for in situ applications and solution-based assays. Nilsson et al., Science 265:2085-2088 (1994), herein incorporated by reference. A padlock probe consists of two target-complementary regions at the 3' and 5' ends and a generic spacer region. When the 3' and 5' terminal regions are juxtaposed on a target DNA sequence, the probe ends can be joined by a DNA ligase to form a circular molecule that is catenated with the target strand. Because these probes remain localized at the target sequences and cannot be easily washed off, they were named "padlock probes."

A problem associated with most exponential amplification methods, including CRCA, is the occurrence of background amplification. Background amplification represents both a problem and a limitation for most amplification methods that employ two primers. One reason that background amplification is not desired is that it can be a source of false positive results. Typically, the RCA and CRCA reactions produce products that are multimers of head to tail tandem repeats. However, background products have been reported, consisting of repeats of a linear target molecule that includes the two primer binding sites, the intervening sequence and additional sequence of the template molecule flanking the primer-binding site. Background amplification products are especially problematic for real-time detection instruments because these instruments cannot distinguish between the fluorescent signal generated by background amplification products and the fluorescent signal generated by the intended amplification product.

There are several reported methods for reducing the occurrence of background amplification. One such method employs an enrichment step of the circular nucleic acid probe prior to amplification. WO 00/36141, herein incorporated by reference.

The present invention improves on the existing methods for amplifying padlock probes by eliminating or delaying the appearance of artifact products that cause false positive results and improving detectability of the probes. The present invention also increases the sensitivity and speed of the assay.

To achieve these and other advantages, and in accordance with the principles of the present invention as embodied and described herein, the present invention, in one aspect, provides a nucleic acid amplification method comprising: (a) providing a closed circular padlock probe molecule; a target nucleic acid molecule; a forward primer; a reverse primer; dNTPs; and a first DNA polymerase to form a reaction mixture; (b) creating a multi-tailed complex; (c) activating a second DNA polymerase, wherein the second DNA polymerase is thermostable; and (d) thermocycling the multi-tailed complex.

The present invention also provides a nucleic acid molecule amplification kit comprising: (a) a forward primer and a reverse primer; (b) a ligase enzyme; (c) a first polymerase enzyme; (d) a linear padlock probe molecule, wherein the padlock probe comprises a 3' terminal region, a 5' terminal region, and a spacer region, wherein the spacer region contains binding sites for the forward primer and the reverse primer; and (e) a second polymerase enzyme, wherein the second polymerase enzyme is a thermostable enzyme and wherein the second polymerase enzyme is not the same enzyme as the first polymerase enzyme.

Also provided by the present invention is a method for detecting a target nucleic acid molecule in a sample comprising: (a) providing a target nucleic acid molecule, a linear padlock probe molecule, a ligase enzyme, a forward primer, a reverse primer, dNTPs, and a first DNA polymerase; (b) creating a closed circular padlock probe molecule; (c) creating a multi-tailed complex from the closed circular padlock probe molecule; (d) activating a second DNA polymerase; (e) thermocycling the multi-tailed complex with the second DNA polymerase; and (f) detecting the amplification product of the multi-tailed complex.

The present invention further provides a method for detecting a target nucleic acid molecule in a sample comprising: (a) providing a target nucleic acid molecule, a closed circular padlock probe molecule topologically linked to the target nucleic acid molecule, a forward primer, a reverse primer, dNTPs, and a first DNA polymerase; (b) creating a multi-tailed complex from the closed circular padlock probe molecule; (c) activating a second DNA polymerase; (d) thermocycling the multi-tailed complex with the second DNA polymerase; and (e) detecting the amplification product of the multi-tailed complex.

The present invention further provides a method for detecting a plurality of target nucleic acid molecules in a sample comprising: (a) providing a plurality of target nucleic acid molecules, a plurality of linear padlock probe molecules capable of annealing to a plurality of distinct target nucleic acid molecule, a ligase enzyme, dNTPs, and a first DNA polymerase; (b) creating at least two closed circular nucleic acid molecules, wherein each of the closed circular nucleic acid molecules is topologically linked to a distinct target nucleic acid molecule; (c) providing, for each member of the at least two closed circular nucleic acid molecules, a forward primer and a reverse primer; (d) creating a multi-tailed complex for each of the distinct target nucleic acid molecules; (e) activating a second DNA polymerase; (f) thermocycling the at least two distinct multi-tailed complexes with the second DNA polymerase; and (g) detecting the amplification products of the at least two distinct multi-tailed complexes.

The present invention also provides a closed tube nucleic acid molecule amplification method comprising: (a) providing a target nucleic acid molecule, a ligase enzyme; a forward primer; a reverse primer; dNTPs; and a first DNA polymerase in a reaction tube; (b) sealing the reaction tube; (c) creating a closed circular padlock probe molecule; (d) creating a multi-tailed complex from the closed circular padlock probe molecule; (e) activating a second DNA polymerase, wherein the second DNA polymerase is a thermostable DNA polymerase; and (f) thermocycling the multi-tailed complex.

The present invention also provides a padlock probe amplification primer comprising any of the following sequences: 5'-actagagctgagaca-3' (SEQ ID NO: 1); 5'-actagagttcagaca-3' (SEQ ID NO: 2); 5'-actagagctgagacatgacga-3' (SEQ ID NO: 3); 5'-actagagttcagacatgacga-3' (SEQ ID NO: 4); 5'-actagagctgagacatgacgagtc -3' (SEQ ID NO: 5); 5'-actagagttcagacatgacgagtc-3' (SEQ ID NO: 6); 5'-actagagctgagacatgacgagtcgca-3' (SEQ ID NO: 7); or 5'-actagagttcagacatgacgagtcgca-3' (SEC) ID NO: 8), wherein at least one nucleotide base contained in the primer is a non-informative base analog.

Further provided by the present invention is a padlock probe amplification primer of 15 to 75 nucleotides wherein at least one nucleotide base contained in the primer is a non-informative base analog.

BRIEF DESCRIPTION OF THE DRAWINGS

The accompanying drawings, which are incorporated in and constitute a part of this specification, illustrate various embodiments and/or features of the invention and together with the description, serve to explain the principles of the invention. In the drawings:

FIG. 4A provides an illustration of the change in fluorescent signal measured over time for a polymerase chain reaction amplification using Deep Vent™ polymerase of differing concentrations of a padlock probe. FIG. 4B provides an illustration of the change in fluorescent signal measured over time for a circular probe amplification of differing concentrations of a padlock probe using Deep Vent™ polymerase and Bst LF.

FIG. 5A provides an illustration of the change in fluorescent signal measured over time for a polymerase chain reaction amplification using Platinum Taq™ of differing concentrations of a padlock probe. FIG. 5B provides an illustration of the change in fluorescent signal measured over time for a circular probe amplification of differing concentrations of a padlock probe using Platinum Taq™ DNA polymerase and Bst LF.

DETAILED DESCRIPTION OF THE INVENTION

A. Rolling Circle Amplification

Figure 1:
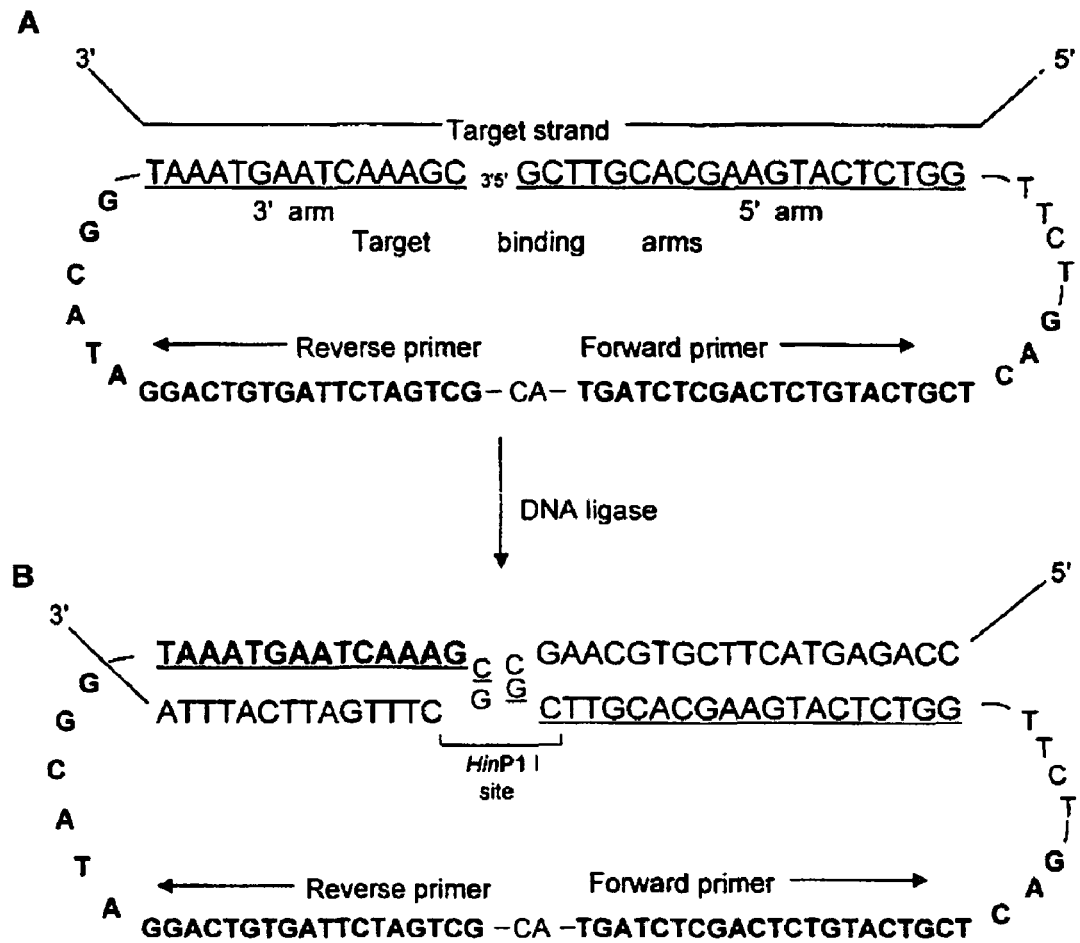
FIG. 1A provides a schematic of a padlock probe annealed to a target nucleic acid molecule (SEQ ID NO: 9).
FIG. 1B provides a schematic of a padlock probe that has been ligated to form a closed circular nucleic acid molecule (SEC) ID NO: 20).

The process of rolling circle replication (amplification) is used by many viruses and plasmids to replicate their genome. It is understood that as used in the present invention, the terms replication and amplification are intended to be used interchangeably. During viral rolling circle amplification, a DNA polymerase, in conjunction with accessory factors such as helicases and/or single-strand DNA binding proteins that help displace the "daughter" strand tail, advances repeatedly around the circular nucleic acid molecule, which can be several kilobases in size. This results in the production of individual or tandem single-strand copies of the genome, which are then processed to form unit length circles.

Rolling circle amplification has been performed in vitro using primed synthetic circular single-stranded DNA templates smaller than 100 bases. Fire and Xu, Proc. Nat'l Acad. Sci. (USA) 92:4641-4645 (1995), U.S. Pat. Nos. 6,096,880, 6,077,668, 5,854,033 and 5,714,320, all of which are herein incorporated by reference. RCA can also be used to amplify circular RNA templates. Long single-stranded tails containing hundreds of tandem copies of the template can be generated by several polymerases, some without accessory factors. This process is named rolling circle amplification and is an isothermal linear amplification of the initial DNA template.

Any DNA polymerase that can perform rolling circle amplification is suitable for use in RCA. The ability of a polymerase to carry out rolling circle amplification can be determined by using the polymerase in a rolling circle amplification assay such as those described in Fire and Xu, Proc. Natl. Acad. Sci. (USA) 92:4641-4645 (1995), herein incorporated by reference.

DNA polymerases that are capable of displacing the strand complementary to the template strand, a process called strand displacement, are generally used in rolling circle amplification. Strand displacement allows for the synthesis of multiple tandem copies of the circular vector. Occasionally, strand displacement factors are used in conjunction with the polymerase to effectuate strand displacement. However, it is understood that at least some polymerases, such as Bst, are capable of strand displacement without a strand displacement factor. Bst is derived from *Bacillus stearothermophilus* N3468. Aliotta et al., Genet. Anal. 12(5-6):185-95 (1996); Phang et al., Gene 163(1):65-8 (1995) herein incorporated by reference.

Typically, the polymerase enzyme used in RCA lacks a 5' to 3' exonuclease activity because, if present, it might destroy the synthesized strand. It is also typical that the DNA polymerase used is highly processive. As used herein, the term "processive" refers to the ability of a polymerase enzyme to carry out strand synthesis without disassociating from the template strand.

Polymerase enzymes suitable for use in RCA include, but are not limited to, DNA polymerase I, Klenow fragment of DNA polymerase I, T4 DNA polymerase, T7 DNA polymerase, Taq™ polymerase, Vent™ polymerase, Deep Vent™ polymerase, φ29 polymerase, Bst polymerase, and Bst Large Fragment (Bst LF). Bst LF is described by Lu et al., Biotechniques 11(4):464-466 (1991), Riggs et al., Biochim. Biophys. Acta 1307(2):178-86 (1996), both of which are herein incorporated by reference. Bst LF is also commercially available from New England Biolabs.

A rolling circle amplification mechanism has been previously reported to amplify small DNA circles or ligated padlock probes by several thousand fold. Lizardi et al., Nat. Genet. 19(3):225-232 (1998). In these approaches, a single primer is hybridized to the circular template and extended by a DNA polymerase around the circle. Upon reaching the primer, the polymerase displaces the primer and continues repeatedly around the circle to generate a long single-stranded tailed product. As used herein, the term "tailed product" refers to a nucleic acid molecule having a structure like that of FIG. 2A.

RCA reactions have been described where, rather than using a first primer, the target sequence itself is used as a primer. After hybridization and ligation, one may degrade the single-stranded nucleic acid with a single stranded exonuclease (e.g., DNase or RNase) leaving the remaining double stranded portion to act as a primer. The RCA technique does not employ a second primer. Because single-primer amplification is a linear process, it is typically used to detect cytological or other solid-phase sample preparations. Lizardi et al., Nat. Genet. 19(3):225-232 (1998), herein incorporated by reference. Depending on the DNA polymerase one uses to amplify, sufficient exonuclease activity may be inherently present, thereby obviating the use of a primer in RCA.

B. Cascade Rolling Circle Amplification (CRCA)

CRCA combines the technology of RCA, two primer amplification and padlock probes. The CRCA technology is being commercially developed by Molecular Staging, Inc. (New Haven, Conn.) through its Rolling Circle Amplification Technology (RCAT™).

A padlock probe consists of two target-complementary regions at the 3' and 5' ends connected by a spacer region such that, when properly annealed to the target sequence, the two target complementary ends are joined by a DNA ligase to form a circular probe that is topologically linked to the target. Since these probes cannot be easily washed off, they provide a highly specific detection technique with low background. The sensitivity of padlock probes can be enhanced several hundred fold by subjecting them to RCA upon addition of a unique primer and a strand-displacing DNA polymerase. The RCA products can then be detected by direct incorporation of label, by use of a labeled antibody to a hapten incorporated during DNA synthesis, or by hybridization to a labeled detection probe. U.S. Pat. No. 5,912,124, which is herein incorporated by reference, describes padlock probes.

While several DNA polymerases are capable of supporting an RCA reaction, Bst DNA polymerase (large fragment) (Bst LF) is the DNA polymerase most often used in the CRCA reaction. Bst LF is commercially available from several commercial vendors, such as New England Biolabs (Beverly, Mass.) or Epicentre (Madison, Wis.). Other polymerase enzymes reported to be suitable for use in a CRCA reaction include, but are not limited to, Vent™, Deep Vent™ and φ29.

To prepare a padlock probe, a linear open circle probe is hybridized to the target sequence for ligation to occur. The basic structure of a padlock probe is depicted in FIG. 1. The probe consists of two target-complementary regions in the 3' and 5' terminal regions connected by a spacer region containing binding sites for amplification primers. The probe can be circularized when the terminal 3' hydroxyl and 5' phosphate groups are juxtaposed on the target. The ligation of the terminal 3' hydroxyl and 5' phosphate groups can be done enzymatically using, for example, a DNA ligase enzyme or it can be done chemically. Generally, the ligation reaction is performed using a DNA ligase enzyme.

After ligation, a closed circular nucleic acid is formed. A first (forward) primer can then anneal to a forward primer binding region in the circularized probe. A second (reverse) primer may be present from the start of the amplification reaction, or it can be added at any time as it does not anneal until after the first primer is extended. The forward primer is generally at least 10 bases in length. More commonly, the forward primer ranges from 15 to 30 bases in length. The reverse primer is generally at least 10 bases in length. More commonly, the reverse primer ranges from 15 to 30 bases in length.

A DNA polymerase with strand displacing activity catalyzes the primer extension. Typically, the DNA polymerase is the Bst LF DNA polymerase. The DNA polymerase enzyme generates a tailed product of many tandem repeats of the target sequence and accordingly many primer binding sites for the second reverse primer. In addition to the DNA polymerase, other reaction components are added. The addition of these other reaction components are known to persons of skill in the art for the purposes of optimizing this reaction. These other reaction components include dNTPs, buffer, salts (e.g., magnesium sulfate, potassium chloride, or ammonium sulfate) and surfactants (e.g., non-ionic detergents such as Triton X-100 (t-Octylphenoxypolyethoxyethanol)).

C. Polymerase Chain Reaction (PCR)

PCR represents another target amplification procedure. Saiki et al., Science 230:1305-1354 (1980). In this procedure, a specific segment of nucleic acid is amplified using two primers, one for each strand, which are used to direct selective chain amplification by a polymerase enzyme. U.S. Pat. Nos. 4,683,202 and 4,683,195, both of which are herein incorporated by reference. As each primer is extended, it creates a copy of the original template. Thermal denaturation of these copies from the original template results in four strands that can be replicated in the next cycle.

Today, the PCR reaction is conducted using thermal stable polymerase enzymes. These enzymes, their use and sources for obtaining them are known to persons of skill in the art. The thermal stable polymerase enzymes most often used include Vent™, Deep Vent™, Pfu, as well as versions of Taq™, such as AmpliTaq™, AmpliTaq™ Gold, Platinum Taq™ and ExTaq™.

D. Circular Probe Amplification (CPA)

The circular probe amplification (CPA) method of the present invention combines the processes of CRCA and PCR to achieve a super-exponential amplification reaction. In this reaction, a linear padlock probe is circularized and amplified in the presence of two primers for a brief period using a first DNA polymerase capable of strand displacement, most typically Bst LF.

As used herein, the term "probe" refers to a nucleic acid molecule that hybridizes (anneals) to a target nucleic acid molecule, but is not itself extended by a polymerase enzyme. A "probe" is an oligonucleotide capable of binding to a target nucleic acid of complementary sequence through one or more types of chemical bonds, through complementary base pairing, or through hydrogen bond formation. The probe may include natural (i.e., A, G, C, or T) or modified bases (7-deazaguanosine, inosine, etc.). In addition, bases in a probe may be joined by a linkage other than a phosphodiester bond, so long as it does not prevent hybridization. Thus, oligonucleotide probes may have constituent bases joined by peptide bonds rather than phosphodiester linkages. A "primer", as used herein, however, not only hybridizes (anneals) to the probe molecule, but is extended by a polymerase enzyme.

The amplification period is long enough to generate a large number of new primer sites, but not long enough to generate a detectable product. This can be followed by a step to denature the first polymerase enzyme. The amplification product is further amplified using a second, typically a thermal stable, polymerase enzyme and a thermal cycling process. The cycling phase of the process is not classical PCR in the sense that a unique size amplicon is not generated, but rather a range of products is generated owing to the large number of primer sites present on the long tandem repeats generated during the initial rolling circle amplification phase. This is further contrasted to standard PCR and other target amplification techniques used in DNA diagnostics because only the probe molecule is amplified, not the target DNA.

To prepare a padlock probe, a linear open circle probe is hybridized to the target nucleic acid for ligation to occur. As used herein, the term "target nucleic acid" refers to the nucleic acid molecule to which the padlock probe hybridizes. The target nucleic acid can be RNA or DNA, single-stranded or double-stranded. The target nucleic acid can be any form of a nucleic acid molecule including, but not limited to, a plasmid or fragment thereof, genomic DNA or fragment thereof, viral DNA or fragment thereof, viral RNA or fragment thereof, messenger RNA or fragment thereof, mitochondrial DNA or fragment thereof, chromosomal DNA or fragment thereof, etc. When the target nucleic acid is double-stranded, the target nucleic acid is typically denatured to allow for the padlock probe to hybridize to the target nucleic acid.

The basic structure of a padlock probe is depicted in FIG. 1. The probe, which has the features of the CRCA probe, consists of two target-complementary regions in the 3' and 5' terminal regions connected by a spacer region containing binding sites for amplification primers. The probe can be circularized when the terminal 3' hydroxyl and 5' phosphate groups are juxtaposed on the target. The ligation of the terminal 3' hydroxyl and 5' phosphate groups can be done enzymatically using, for example, a DNA ligase enzyme or it can be done chemically. The ligation reaction is usually performed using a DNA ligase enzyme.

It is understood that the circularization of the padlock probe may be performed by any one of a number of methods including, but not limited to, gap-filling or spacer oligonucleotide ligation. As used herein, gap-filling refers to the circularization of an open circle nucleic acid probe via the synthesis of a nucleotide sequence to link the terminal ends of the open circle nucleic acid probe. In this regard, the open circle nucleic acid probe is reacted with the required dNTPs, ligase and a DNA polymerase. As used herein, "spacer oligonucleotide ligation" refers to the insertion of one or more previously synthesized oligonucleotide sequences into the gap between the 5' and 3' ends of the open circle nucleic acid probe. The ends of the spacer are then ligated with the ends of the open circle nucleic acid probe using, for example, a ligase enzyme or chemical reaction. When one or more spacer oligonucleotide are utilized, they may be, for example, ligated in tandem to fill the gap between the 5' and 3' ends of the open circle nucleic acid probe.

As used herein, the term dNTPs refers to dATP (deoxyadenosine triphosphate), dGTP (deoxy-guanine triphosphate), dCTP (deoxy-cytosine triphosphate), dTTP (deoxy-thymine triphosphate) and base derivatives such as dIPT (deoxy-inosine triphosphate), dUTP (deoxy-uracil triphosphate) and other purine and pyrimidine base derivatives.

The 5' terminal region is long enough to provide a relatively strong and specific annealing. Generally, 20 bases is long enough for use in the present invention. However, strong and specific annealing can be obtained with a 5' terminal region having as few as 10 bases. Under the most common embodiment, the 5' terminal region is at least 20 bases.

Stringency conditions in nucleic acid hybridizations can be readily determined by those having ordinary skill in the art based on, for example, the length and composition of the nucleic acid. In one embodiment, moderate stringency is herein defined as a nucleic acid having 10, 11, 12, 13, 14, 15, 16, or 17 contiguous nucleotides identical to any of the sequences of the padlock probes of the present invention, or a complement thereof. Similarly, high stringency is hereby defined as a nucleic acid having 18, 19, 20, 21, 22, or more contiguous identical nucleotides, or a longer nucleic acid having at least 80, 85, 90, 95, or 99 percent identity with any of the sequences of the padlock probes of the present invention; for sequences of at least 50, 100, 150, 200, or 250 nucleotides, high stringency may comprise an overall identity of at least 60, 65, 70 or 75 percent.

Generally, nucleic acid hybridization simply involves providing a denatured nucleotide molecule or probe and target nucleic acid under conditions where the probe and its complementary target can form stable hybrid duplexes through complementary base pairing. The nucleic acids that do not substantially form hybrid duplexes are then washed away leaving the hybridized nucleic acids to be detected, typically through detection of an attached detectable label. It is further generally recognized that nucleic acids are denatured by increasing the temperature or decreasing the salt concentration of the buffer containing the nucleic acids. Under lower stringency conditions (e.g., low temperature and/or high salt), hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency.

As used herein, the percent identity between any of the sequence provided herein and a potential hybridizing variant can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess (*Nucl. Acids Res.* 14:6745, 1986), as described by Schwartz and Dayhoff (eds., *Atlas of Protein Sequence and Structure*, National Biomedical Research Foundation, pp. 353-358, 1979); (2) a penalty of 3.0 for each gap and an additional 0.10 penalty for each symbol in each gap; and (3) no penalty for end gaps.

Alternatively, basic protocols for empirically determining hybridization stringency are set forth in section 2.10 of *Current Protocols in Molecular Biology* edited by F. A. Ausubel et al., John Wiley and Sons, Inc. (1987). Stringency conditions can be determined readily by the skilled artisan. An example of moderate stringency hybridization conditions would be hybridization in 5×SSC, 5×Denhardt's Solution, 50% (w/v) formamide, and 1% SDS at 42° C. with washing conditions of 0.2×SSC and 0.1% SDS at 42° C. An example of high stringency conditions can be defined as hybridization conditions as above, and with washing at approximately 68° C., in 0.1×SSC, and 0.1% SDS. The skilled artisan will recognize that the temperature and wash solution salt concentration can be adjusted as necessary according to factors such as the length of the probe.

Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence).

Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, Jan. 12-19, 1985); Smith et al. (*Genetic Engineering: Principles and Methods*, Plenum Press, 1981); Kunkel (*Proc. Natl. Acad. Sci.* USA 82:488, 1985); Kunkel et al. (*Methods in Enzymol.* 154:367, 1987); and U.S. Pat. Nos. 4,518,584 and 4,737,462, all of which are incorporated by reference.

Although the 3' terminal region can be as long as the 5' terminal region, according to one embodiment, the 3' terminal region is shorter (10-15 bases in length). The specific, but weaker annealing, provided by a shorter 3' terminal region improves ligase discrimination. Ligase discrimination is also improved by base mismatches at the 3' terminus or 5' terminus. However, base mismatches at the 3' terminus are more inhibitory to ligation than those at the 5' terminus. Luo et al., Nucleic Acids Res. 24(15):3071-8 (1996), herein incorporated by reference. The base mismatch can be at any location in the terminal region. However, where detection of a base mutation is being performed, the mismatch is at the location of the base mutation. Techniques to enhance binding and discrimination, and thus overall sensitivity, are set forth, for example, in U.S. Pat. No. 5,494,810, herein incorporated by reference.

The spacer region may be of variable length, although it is not required. When used, the spacer region is long enough to allow the two terminal regions to efficiently hybridize to the target nucleic acid. The spacer region can be at least 54 bases in length. For small double-stranded DNA circles of less than 150 base pairs, polymerase displacement of the tails is reported to be enhanced compared to larger templates because of the strain associated with these small circular DNA molecules. Baner et al., Nucleic Acids Res. 26(22): 5073-5078 (1998), herein incorporated by reference.

Typically, the spacer region contains a binding site for at least one primer, the forward primer. The spacer region may further contain the sequence of the reverse primer. In one embodiment, the binding site for the forward primer can contain a "primer-terminal spacing region" from 0 bases to no upper limit. As used herein, the term "primer-terminal spacing region" refers to the inclusion of nucleotide bases between the primer region and the terminal region. Likewise, the reverse primer sequence and the 3' terminal region can contain a primer-terminal spacing region from 0 bases to no upper limit.

The primers are in opposite orientations in the probe. As depicted in FIG. 1, the binding site for the forward primer and the sequence of the reverse primer may be separated by a "primer-spacing region." As used herein, the term "primer-spacing region" refers to the inclusion of nucleotide bases between the forward and reverse primer regions. This primer-spacing region generally ranges from 0 to 10 bases. It is understood, however, that a longer primer-spacing region can be used.

In one embodiment, the primers binding to the spacer region are identical to primers and spacer regions for different open circle probes, thus allowing generic primers to be used for the CRCA phase and PCR phase amplification of at least a portion of the padlock probe.

The ligation can be catalyzed by a thermophilic ligase, such as Ampligase™ (Epicentre Technologies, Madison, Wis.) or Taq™ DNA ligase (New England Biolabs, Beverly, Mass.). However, other ligases, including thermolabile ligases, are effective in the present invention. It is understood that the ligase reaction may require additional ingredients depending on the specific ligase chosen. There are two main types of ligases, those that are ATP-dependent and those that are NAD-dependent. For example, NAD is added to the ligase reaction for Ampligase™, *E. coli* ligase and Taq™ DNA ligase. Most ligases use Mg++. Commercial vendors often supply the ligase enzyme with a concentrated reaction buffer that contains all of the necessary ingredients for the ligase reaction to occur. The ligase and ligation conditions can be optimized to limit the frequency of ligation of single-stranded termini. In one embodiment, the vendor supplied reaction buffer is used. In another embodiment, especially where a closed tube system is employed, the vendor supplied reaction buffer may not be suitable for use because it may not contain all of the necessary ingredients to allow both the ligase enzyme and polymerase enzyme to be active in the reaction mixture. In this situation, the selection of reaction ingredients to allow for both the ligase and amplification reactions to run is well within the skill of a person of ordinary skill in the art.

After ligation, a closed circular nucleic acid molecule is formed. The present invention then adds a forward primer, which anneals to a forward primer binding region in the circularized probe. The forward primer can be 10 bases in length, 15 to 30 bases in length, or longer.

In one embodiment, the forward primer or reverse primer contains at least one non-informative base. As used herein, the term "non-informative base" refers to a nucleotide base that has been modified such that it acts as a stop site for DNA polymerases. Accordingly, non-informative bases can be used during CPA to eliminate or reduce amplification artifacts. Non-informative bases suitable for such use include, but are not limited to, nitropyrrole and nitroindole. These non-informative sites can be incorporated into any position in the forward or reverse primer, and can be used in combination. For example, the forward or reverse primer can contain two or more nitropyrrole bases, two or more nitroindole bases, or one or more nitropyrrole bases and one or more nitroindole bases. An alternative non-informative base that can be used in the present invention are polarity switches. As used herein, the term "polarity switch" refers to two bases linked by a 3'-3' and a 5'-5' phosphodiester bond instead of the normal 5'-3' phosphodiester bond. The polarity switch may occur at between any bases in a primer. Such modification are strong stop sites for polymerases, including Bst LF.

Conventionally, non-informative bases are only used in hybridization probe molecules and are not used in amplification primer molecules because they effectively stop DNA synthesis or amplification. However, in the present CPA reaction, DNA amplification is still possible using primers containing non-informative bases because of the multitude of primer initiation sites that are present on the multi-tailed complex.

The forward primer is extended by a first DNA polymerase with strand displacing activity that catalyzes the primer extension. As the forward primer is extended, second (reverse) primer binding sites are formed.

Any DNA polymerase enzyme that can perform rolling circle amplification is suitable for use in CPA. The ability of a polymerase to carry out rolling circle amplification can be determined by using the polymerase in a rolling circle amplification assay such as those described in Fire and Xu, Proc. Natl. Acad. Sci. (USA) 92:4641-4645 (1995). In one embodiment, the polymerase enzyme used in CPA lacks a 5' to 3' exonuclease activity to reduce the chance of, or to eliminate, the destruction of the synthesized strand. The DNA polymerase may be highly processive.

Polymerase enzymes suitable for use in the first amplification step of CPA include, but are not limited to, DNA polymerase I, Klenow fragment of DNA polymerase I, T4 DNA polymerase, T7 DNA polymerase, Taq™ polymerase, Vent™ polymerase, Deep Vent™ polymerase, φ29 polymerase, Bst polymerase, and Bst LF polymerase. For the first DNA polymerase, Bst LF DNA polymerase is the polymerase enzyme most often used.

Figure 2:
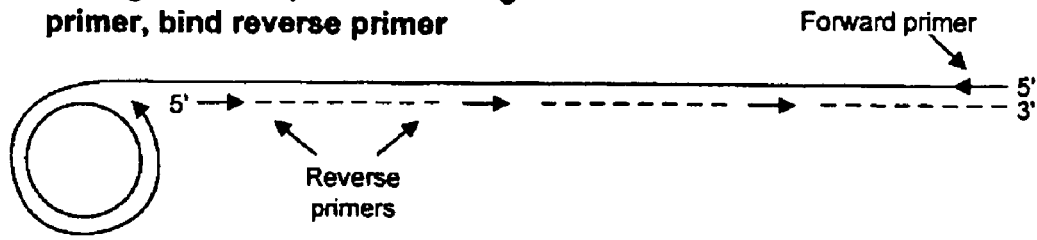
FIG. 2A provides a schematic of rolling circle amplification, FIG. 2B provides a schematic of cascade rolling circle amplification, and FIG. 2C provides a schematic of a polymerase chain reaction amplification of a product from a cascade rolling circle amplification.
Figure 2:
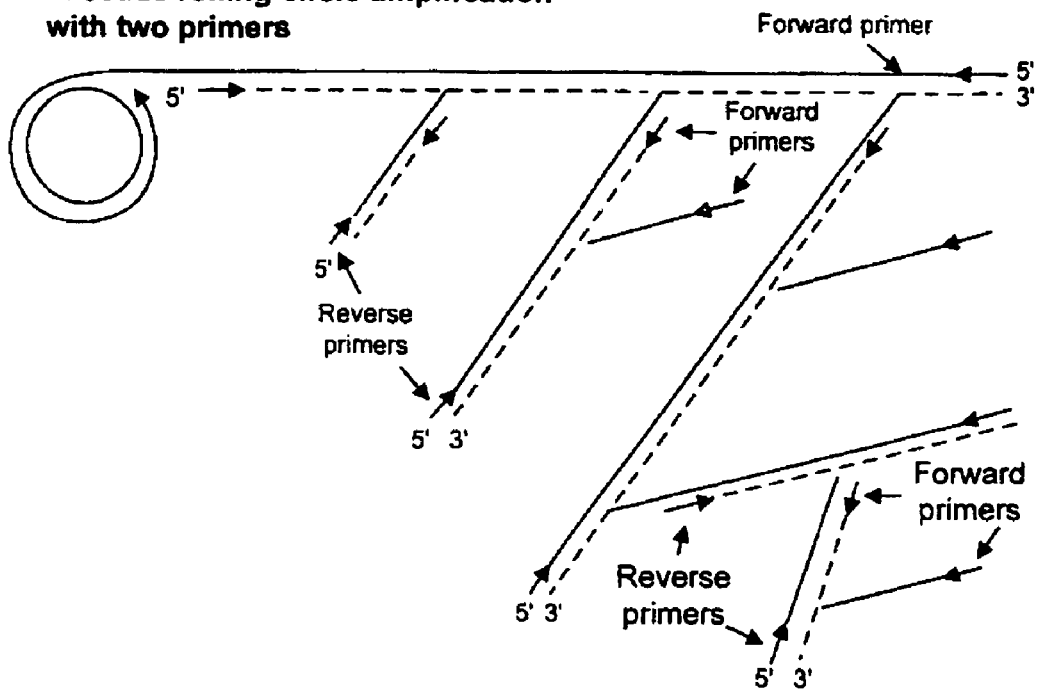
Figure 2:
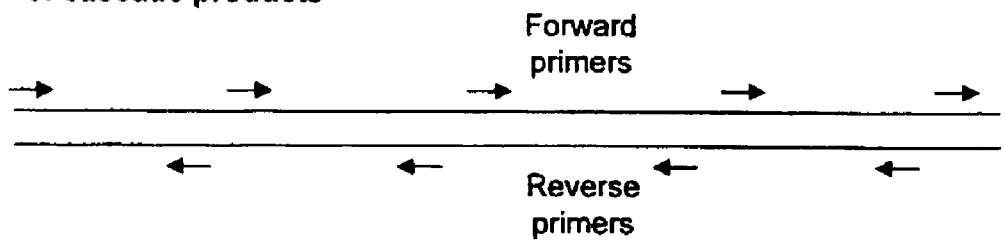

To achieve sufficient sensitivity in a solution-based diagnostic assay and single copy solid-phase based diagnostic assays, the present invention employs a second (reverse) primer that anneals to the reverse primer binding region generated by extension of the first (forward) primer. FIG. 2(B). The reverse primer may be present from the start of the amplification reaction, or it can be added at any time as it does not anneal until after the first primer has been extended. The reverse primer may range from 10 bases in length to 15 to 30 bases in length, or longer.

The second (reverse) primer anneals to the second (reverse) primer binding sites, which are created by the forward primer extension product. The second (reverse) primer is extended by the action of the first DNA polymerase. As these extended second primers form complementary sequences and displace each other, additional 5' tails containing forward (first) primer binding sites are formed. These secondary 5' tails then provide a template for the first (forward) primer. Both forward and reverse primers continue to initiate synthesis on the displaced strand from the previous round of synthesis creating a "multi-tailed complex," which is a large complex of tandem copies of the original padlock probe and its complement in linear form. A schematic of the multi-tailed complex is provided in FIG. 2(B). As shown in this schematic, the "multi-tailed complex" contains hundreds or thousands of individual forward and reverse primer bindings sites, all of which are part of one complex, and all of which stem from an original closed circular nucleic acid probe molecule.

The primer concentration of the forward and reverse primers can range from about 100 nM to about 1 µM, and can be from about 250 to about 500 nm. Although employing high concentrations of primers can be advantageous, too high of a primer concentration could drive the reaction to generate unacceptable levels of false signals. Generally, at least one of the primers is detectably labeled.

In addition to the first DNA polymerase, other reaction components are added. The addition of these other reaction components are known to persons of skill in the art, and include dNTPs, buffer, salts (e.g., magnesium sulfate, potassium chloride, or ammonium sulfate) and surfactants (e.g., non-ionic detergents such as Triton X-100).

Strand displacement can be facilitated through the use of a strand displacement factor, such as helicase and/or single-stranded DNA binding proteins. Strand displacement factors useful in RCA include BMRF1 polymerase accessory subunit (Tsurumi et al., J. Virology 67(12):7648-7653 (1993), herein incorporated by reference), adenovirus DNA-binding protein (Zijderveld and van der Vliet, J. Virology 68(2):1158-1164 (1994), herein incorporated by reference), herpes simplex viral protein ICP8 (Boehmer and Lehman, J. Virology 67(2): 711-715 (1993); Skaliter and Lehman, Proc. Natl. Acad. Sci. (USA) 91(22):10665-10669 (1994), both of which are herein incorporated by reference), single-stranded DNA binding proteins (SSB; Rigler and Romano, J. Biol. Chem. 270:8910-8919 (1995), herein incorporated by reference), and calf thymus helicase (Siegal et al., J. Biol. Chem. 267:13629-13635 (1992), herein incorporated by reference).

The amplification period using the first DNA polymerase is usually long enough to generate a large number of new primer sites in the multi-tailed complex, but typically not long enough to generate a detectable product. As used herein, the term "detectable product" refers to an amplification product that is detectable through, for example, direct visualization on a agarose gel stained with ethidium bromide (typically less than 10 ng cannot be detected in an ethidium bromide stained agarose gel) or, where the amplification product is being measured by an instrument, the amplification product signal is not measurably above background. A detectable product is usually not generated until the amplification is in the logarithmic (or exponential) phase. Generally, an incubation period of from about 1 to about 30 minutes at about 50 to about 70° C. is long enough to generate a sufficient number of new primer sites for the present invention. The incubation period can also be from about 3 to about 20 minutes at about 50 to about 70° C., or about 10 minutes at about 65° C. It is understood that as used in the present invention, when the term "about" is used to modify a first parameter or range, but is not used to modify another parameter or range, the second parameter or range was intended to be modified by the term about. All of the times, temperatures, concentrations, volumes and masses used in the present invention are not absolute values, rather they are values that can be, and are routinely, manipulated by those of skill in the art.

It is understood that the temperature of the incubation time can affect the length of time needed to generate sufficient primer sites. Polymerase enzymes generally have an optimal set of conditions, including temperature, at which they operate. Bst LF, for example, operates at peak efficiency from about 63 to about 67° C. Although Bst LF is thermostable, it is a moderately thermostable enzyme. At temperatures greater than about 75° C., Bst LF is denatured.

It is understood that a person of skill in the art can manipulate the reaction conditions of the present invention to slow down or even speed up the reaction. For example, slight variations in buffer conditions or primer concentrations can also affect the reaction. Moreover, a person of skill in the art can perform genetic or chemical modifications to a polymerase enzyme to alter the characteristics of the polymerase enzyme. Such modifications are within the scope of the present invention.

Even a single round of amplification using the first polymerase results in a large amplification of the circularized probe molecule, orders of magnitude greater than a single cycle of PCR replication or other amplification technique in which each cycle is limited to a doubling of the number of copies of the target sequence.

After the initial amplification of the circular probe, the first DNA polymerase can be denatured, although this is optional. Usually, the first DNA polymerase is heat denatured. However, chemical denaturation, such as phenol:chloroform extractions can also be performed. As another alternative, the amplification product can be purified away from the first DNA polymerase using, for example, ethanol precipitation.

A second DNA polymerase is then used to amplify the multi-tailed complex. The second DNA polymerase can be a thermostable (also referred to as thermal stable) polymerase enzyme. These enzymes, their use and sources for obtaining them are known to persons of skill in the art. Suitable thermostable polymerase enzymes include polymerase enzymes derived from *Thermus aquaticus*, such as Taq™, AmpliTaq™, AmpliTaq™ Gold, Platinum Taq™ and Ex Taq™, *Pyrococcus* species, such as Deep Vent™, *Thermococcus litoralis*, such as Vent™, and *Pyrococcus furiosus*, such as Pfu and PfuTurbo. As used herein, a polymerase enzyme is considered to be derived from an organism when the polymerase enzyme itself has been purified from the organism. Also within the definition of derived is where the gene encoding the polymerase enzyme has been isolated from the organism, cloned into another organism and that recombinant enzyme purified. Such recombinant polymerase that have been further modified through genetic manipulations, are also considered to be derived from the named organism.

Under another embodiment, the second DNA polymerase is an antibody-inactivated polymerase or a chemically-inactivated polymerase. Antibody-inactivated polymerases, such as PfuTurbo, and Platinum Taq™, are inactive until they are heated to a temperature set by the manufacturer of the polymerase enzyme. During this activation step, for example, Platinum Taq™ becomes active by the disassociation of an inactivating antibody from the polymerase. Chemically-inactivated polymerases, e.g., AmpliTaq™ Gold, are inactive until the enzyme has been heated to a temperature set by the manufacturer of the polymerase enzyme. U.S. Pat. No. 5,545, 522, herein incorporated by reference. At this temperature, a chemical bond that normally prevents the polymerase enzyme from performing DNA synthesis is broken and the polymerase enzyme becomes active.

Under one embodiment, the second polymerase is added to the reaction mixture after the first polymerase has been denatured. As used herein, the term "denature" refers to the inactivation of the first polymerase through such mechanisms as heat denaturation, chemical denaturation and the like. Alternatively, the first and second polymerase enzymes are added as part of the initial reaction mixture. Generally, however, the second polymerase is not active until after the first polymerase has been denatured.

The second polymerase then uses the same forward and reverse primers to exponentially amplify the multi-tailed complex generated by the first polymerase. Because the multi-tailed complex contains multiple primer binding sites, when amplified using a thermal cycling reaction, the reaction product is of variable length. This reaction is also far faster than traditional PCR, which only employs two primer binding sites in its reaction for any given amplicon.

In one embodiment, the first primer is a "lipped primer." As used herein, the term "lipped primer" refers to a primer molecule whose 5' terminal sequence does not hybridize to the padlock probe. Such lipped primers further enhance DNA polymerase displacement by destabilizing the 5' end of the primer. Once initiated, the ever-growing tail acts to provide the same function. The lip also decreases or prevents the primer from being degraded instead of displaced. The use of such lipped primers is particularly useful when the DNA polymerase has a 5'→3' exonuclease activity.

The present invention uses generic primers to amplify a probe sequence instead of the target sequence. Generic primers are designed for efficient amplification and primer binding within the spacer region of a padlock probe, and can be used to amplify numerous padlock probes that differ only in the target binding arms. Thus, the same set of primers and conditions for each probe may be used and optimized. It is possible for the sequence of the regions to have an effect on efficiency, but this is very minor. Using generic probes, there is less chance of obtaining false-negative results by having primers that anneal poorly. Heterozygous and polymorphism containing samples may also resist annealing with conventional PCR primers. The generic primers of the present invention reduce the likelihood of false-positive results by being predetermined not to cross-react.

Under one embodiment, the present invention employs a molecular energy transfer mechanism, such as fluorescence energy transfer (FRET) (U.S. Pat. Nos. 5,565,322, 5,532,129, 4,996,143, all of which are herein incorporated by reference), the TAQMAN™ assay (Holland et al., Proc. Natl. Acad. Sci. (USA) 88:7276-7280 (1991), Lee et al., Nucleic Acids Res. 21:3761-3766 (1993), both of which are herein incorporated by reference), energy sink oligonucleotides (U.S. Pat. No. 5,348,853, and Wang et al., Anal. Chem. 67:1197-1203 (1995), both of which are herein incorporated by reference), molecular beacon probes (U.S. Pat. Nos. 5,312,728 and 5,119,801, and Tyagi and Kramer, Nature Biotech. 14:303-308 (1996), all of which are herein incorporated by reference), Scorpion probes (Astra Zeneca), or molecular energy transfer primers (U.S. Pat. Nos. 6,117,635, 6,090,552 and 5,866,336, all of which are herein incorporated by reference) for detecting a nucleic acid molecule. All of these techniques can be used with real-time detection instruments, such as the Prism™ 7700 (ABI/Perkin Elmer, Foster City, Calif.), Prism™ 5500 (ABI/Perkin Elmer, Foster City, Calif.), I Cycler™(Bio-Rad Laboratories, Hercules, Calif.), and Light Cycler™ (Idaho Technology, Inc., Idaho Falls, Id.). Real-time detection instruments measure changes in fluorescent intensity over time. Other techniques for detecting a nucleic acid molecule include direct incorporation of a label, use of a labeled antibody to a hapten incorporated during DNA synthesis, hybridization to a labeled detection probe.

Commercially available BEACON™ probes (Marras et al., Genet. Anal. 14(5-6):151-6 (1999), herein incorporated by reference) and Amplifluor™ primers (Intergen, Purchase, N.Y.) (Nuovo et al., J. Histochem. Cytochem. 47(3):273-80 (1999), herein incorporated by reference) can be used in the present invention. BEACON™ probes and Amplifluor™ primers are used to detect the presence of the amplified product by emitting fluorescence in direct relationship to the number of target molecules.

Molecular beacon probes are detection probes labeled with fluorescent moieties where the fluorescent moieties fluoresce when the detection probe is hybridized. The use of such probes eliminates the need for removal of unhybridized probes prior to label detection because the unhybridized detection probes will not produce a signal. This is especially useful in a multiplex assay.

CPA is amenable for multiplexing, allowing for the simultaneous screening for a variety of pathogens or mutations. In one embodiment, the present invention employs a multiplex detection system that involves the use of labels that either fluoresce at different wavelengths or are colored differently. Using such a system, several targets can be visualized simultaneously in the same sample. Using a combinatorial strategy, many more targets can be discriminated than the number of resolvable fluorophores. Combinatorial labeling provides the simplest way to label probes in a multiplex fashion since a probe fluor is either absent or present. As used herein, the term "combinatorial labeling" refers to the use of a combination of labels in any given probe molecule illustration (by way of illustration, using a set of three distinct labels (e.g., A, B, C), a person of skill in the art can prepare nine different probe molecules that would be differently labeled. With nine different probe molecules, nine different target molecules can be distinguished. Likewise, using a set of three different primer molecules, each containing a distinct label, a person of skill in the art can differentiate nine different target molecules. It is understood that both primers and probes can be used in the same detection system. Image analysis is thus more amenable to automation, and a number of experimental artifacts, such as differential photobleaching can be avoided.

By way of further illustration, and using HIV as an example, a person of skill in the art can design three different probe molecules, each capable of detecting a mutation associated with therapeutic resistance to a different therapeutic agent. Thus, a person of skill in the art can distinguish nine different genotypes of HIV (e.g., AZT resistant or sensitive, stavudine resistant or sensitive, AZT resistant and stavudine resistant, AZT sensitive and stavudine resistant, etc.). By way of an even further illustration, and using viral infection as an example, a person of skill in the art can design three different probe molecules, each capable of detecting a different virus. Thus, a person of skill in the art, running a battery test can determine if a given sample contains, for example, HIV, HCV, or HBV or any combination thereof. It is understood that these illustrations are not intended to, in any way, limit the present invention. Although three primers or probes are described, it is understood that a person of skill in the art can employ any number of primers or probes and that the only limit to the combination of targets that can be differentiated is the number of distinguishable signals that are available to the person of skill in the art.

Under one embodiment of multiplexing, the present invention provides a reaction mixture comprising a mixture of target nucleic acid molecules, and a plurality of linear nucleic acid probe molecules, wherein each member of the plurality of linear nucleic acid molecules is capable of annealing to a distinct target nucleic acid molecule. Under one embodiment, each member of the plurality of linear nucleic acid molecules anneals to a unique target nucleic acid molecule. The linear nucleic acid molecule is then ligated and becomes a closed circular nucleic acid molecule. A distinct forward primer capable of annealing to a forward primer binding region is provided generally for each member of the plurality of closed circular nucleic acid molecules. Likewise, a distinct reverse primer capable of annealing to a reverse primer binding region is provided in the reaction mix for each member of the plurality of closed circular nucleic acid molecules. Also added to the reaction mixture are dNTPs and a first DNA polymerase. The reaction mixture is incubated to create multi-tailed complex for at least two distinct target nucleic acid molecules. A second thermostable DNA polymerase in the reaction mixture is activated. As used herein, the term "activated" refers to either the addition of a second polymerase to the reaction mixture or, where the second polymerase was present in the initial reaction mixture, the activation of the second polymerase. In the case of antibody-inactivated or chemically-inactivated DNA polymerases, such as Platinum Taq™, Pfu Turbo or AmpliTaq™ Gold, the DNA polymerase is activated when the reaction mixture is heated to a temperature set by the manufacturer of the polymerase enzyme. At this temperature, an inactivating factor is released, or in the case of an inactivating chemical bond, the bond is broken. The reaction mixture is then thermocycled to amplify the at least two distinct multi-tailed complexes and the amplification products of the multi-tailed complexes are detected using a real-time detection instrument.

To further multiplex the present invention, different fluorescent labels with different colors emitted may be used on different primers to designate which padlock probe is being amplified, thereby deducing the presence or amount of each of a plurality of target nucleic acid sequences. Thus, for each member of the plurality of closed circular nucleic acid molecules, at least one distinct forward or at least one distinct reverse primer is differentially labeled. For example, a visible or detectable fluorescein label may indicate a particular infectious agent, while a detectable rhodamine label may indicate another and Texan red still another. It is understood that the list is only limited to the extent that there are a finite number of distinct fluorescers. Such a combination may be used to determine which of multiple pathogens is causing a particular set of patient symptoms. Alternatively, the multiple colors could each indicate antibiotic sensitivity or resistance to different antibiotics. Each color would correspond to a unique primer molecule that anneals to a corresponding unique padlock probe molecule.

Immobilized open circle probes are particularly useful for microarrays for detecting sample nucleic acid targets or single nucleotide polymorphisms. The microarray may contain hundreds or thousands of different open circle probes, each tethered to a specific location on a solid support of the microarray. Alternatively, compartmentalized plates, such as multiwell or "microtiter" plates, may hold separate open circle probes in suspension or tethered to beads or the sides of the plate wells. These arrangements have all of the above uses, as well as rapid sequencing of the nucleic acid target and determining hundreds or thousands of polymorphisms and mutations simultaneously. The microarray may also be prepared after CPA by first amplifying the rolling circle followed by hybridizing it to a solid phase microarray having a complementary oligonucleotide attached thereto. Since the CPA complex contains numerous tandem copies of target DNA, it can both bind to the solid phase and other nucleic acids.

Methods for immobilizing nucleic acids to solid-phase substrates are well known to persons of skill in the art. By way of illustration, suitable attachment methods are described by Guo et al., Nucleic Acids Res. 22:5456-5465 (1994), Pease et al., Proc. Nat'l Acad. Sci. (USA) 91(11):5022-5026 (1994) and Khrapko et al., Mol. Biol. (Mosk) (USSR) 25:718-730 (1991), all of which are herein incorporated by reference.

A method for the multiplex image analysis of nucleic acid molecules is described in U.S. Pat. No. 6,007,994, herein incorporated by reference. According to this method, and similar methods, a plurality of differentially labeled oligonucleotides is employed. By use of differentially labeled oligonucleotides, the practitioner is capable of characterizing multiple nucleic acid samples at the same time.

Conventional microarrays have immobilized oligonucleotides thereby performing massive parallel reverse dot blot assays. The signal to noise ratio has been reported to be as high as 5:1. Such a system is not useful for detecting a rare mutation in a mass of normal sequence. By contrast, a padlock probe requires a discriminating enzyme to be formed and thus the detection of a rare mutation in vast excess of normal target sequence is possible.

Strepavidin coated magnetic beads are useful for concentrating and localizing CPA complexes when using biotin labeled dNTPs during primer extension. Likewise, one can use different receptor coated magnetic or non-magnetic beads, which may have a different color or detectable label, to bind CPA complexes formed by a different ligand labeled dNTP.

PCR has an inherent limitation as to the number of different targets that may be simultaneously amplified, as the PCR amplification products are diffusible. By contrast, RCA complexes are linked together and as such are localized at a different address on a microarray. By using barriers between the cells of the microarray, CPA may also be used. This permits simultaneous detection of hundreds to thousands of different targets simultaneously with the same reagent.

Detection technology based on molecular energy transfer that utilizes labeled primers for amplification may also be used such that a fluorescence signal is generated only when the primers are incorporated into the amplification products. Nazarenko et al., Nucleic Acids Res. 25(12):2516-2521 (1997), Nuovo et al., J. Histochem. Cytochem. 47(3):273-80 (1999), and Uehara et al., Biotechniques 26(3):552-8 (1999), all of which are herein incorporated by reference. The use of such primers enables direct fluorescence detection of the amplified DNA, unlike other systems where the signal is affected by the efficiency of a secondary event, such as probe hybridization.

Under one embodiment of the present invention, the amplification primers are molecular energy transfer primers. Molecular energy transfer primers generate a fluorescent signal when the primers are incorporated into the amplification products. Nazarenko et al., Nucleic Acids Res. 25(12):2516-2521 (1997), Nuovo et al., J. Histochem. Cytochem. 47(3): 273-80 (1999), and Uehara et al., Biotechniques 26(3):552-8 (1999), all of which are herein incorporated by reference. The use of such primers enables amplification systems, such as PCR, CRCA and the present CPA, to be performed with homogeneous fluorescence detection in a closed system. Since the need for post-amplification processing is eliminated, the detection signal can be read directly in real time or immediately upon completion of the amplification step.

As in PCR and CRCA, CPA is driven by two primers. Under one embodiment of the present invention, one or both of these primers can be a hairpin primer labeled with a fluorescer-quencher pair. A hairpin primer generates a background fluorescent signal, unless it is incorporated into the amplification product. Incorporation into the amplification products produces a much higher fluorescent signal. Hairpin primers labeled with a fluorescer-quencher pair and their use in the detection of nucleic acid amplification products are described in U.S. Pat. Nos. 6,117,635, 6,090,552, and 5,866,336, all of which are herein incorporated by reference.

Hairpin primers have the following structure from 5' to 3', a first self-binding region, a loop region, a second self-binding region at least partly complementary to the first self-binding region, and a primer region. The first and second self-binding regions are generally long enough to generate a stable double-stranded structure at room temperature. In one embodiment, the regions are only partially complementary, thereby lowering the disassociation temperature of the double stranded structure. At higher temperatures, such as the temperatures used in the polymerase extension reaction, the double stranded structure becomes unstable. The primer is then extended by the polymerase. The use of only partially complementary regions also prevents the primer from causing the double-stranded reaction product to disassociate.

At temperatures higher than about 60-65° C., the hairpin may be unstable making the reaction mixture appear fluorescent. However, upon cooling the mixture, the hairpin configuration returns resulting in a quenching of all unincorporated primer. If no amplification occurs, background fluorescent signals are all that is detected.

The reverse primer is often the only hairpin primer with a fluorescer-quencher pair. Under this embodiment, when the complement strand to the hairpin primer is synthesized, the hairpin stretches out during displacement thereby separating the fluorescent and quenching moieties resulting in fluorescence. The labeled primer(s) are usually present in excess to ensure complete and fast annealing to their respective template DNA(s). Generally, a solution containing 1 µM of labeled primer provides a sufficient excess of primer. Under another embodiment, however, a limiting amount of primer can be used.

To further separate the fluorescent and quenching moiety, a restriction endonuclease cleavage site may be incorporated into the loop region of the hairpin primer. By adding a restriction endonuclease to the complex, before or after it is formed, one cleaves the double stranded complex thereby further separating the fluorescent moiety from the quenching moiety. By further separating the fluorescent moiety from the quenching moiety, the fluorescence level is increased. Such a modification may be employed in a closed tube system or with a hairpin primer where stretching out of the hairpin primer does not sufficiently separate the fluorescent and quenching moiety.

Rather than using a separate forward and reverse primer, one may use a single molecule with both priming activities. For example, one can use a bifunctional or chimeric primer when the 5' ends of both forward and reverse primers were chemically linked to each other. Detection of such a chimeric primer may be performed by numerous methods, including incorporation of a hairpin loop and two energy transfer labels such that when a complement to the primer is formed in CPA, the energy transfer labels are separated resulting in a detectable signal. DNA polymerase generally cannot process across the part of a chimeric molecule containing the unnatural linkage.

Chimeric primers may also be used in present invention as the forward and reverse primers as both are functional moieties on the chimeric primer. Additionally, since the amplified region contains unnatural 3' tails which lack a complementary partner, unusual complexes can form in the later stages of thermal cycling amplification when the bifunctional primer is not in vast excess. For example, upon denaturing and re-annealing, two (+) strands may anneal at their ends such that one 3' end, which cannot be extended by the other one, can be extended to form a dimer of the amplified sequence. This process can repeat many times forming various multimers. A "multimer," as used herein, refers to a nucleic acid sequence containing multiple copies of the oligomer joined end to end. Also, a single strand with two unnatural 3' ends can self-anneal into a spiral which has one extendable 3' end forming a dimer of a sequence being amplified and its complement. This process may repeat along with the previous self annealing dimers to yield a very large complex. Such techniques have uses when large complexes are desirable such as in-situ PCR and arrays. Primer dimers, a well known problem in amplification, may also be controlled using chimeric primers.

Also, in certain situations, where it may be useful to control the molar ratio of primers, chimeric primers may be employed. Alternatively, branched DNA may be used. Branched DNA are created using a variety of linking agents and reactions to add numerous branched oligonucleotides to a DNA backbone such that their 3' ends are free. U.S. Pat. Nos. 5,916,750, 5,124,246; 4,925,785, all of which are herein incorporated by reference. The bound relationship of the primers controls the molar ratios and may aid in reducing the formation of primer dimers. By way of illustration, a three primer chimeric primer was used in the three primer amplification system described in Bhatnagar et al., U.S. Pat. No. 5,593,840, herein incorporated by reference.

Once a multimer has been formed using the methods of the present invention, it can be cleaved by any of a number of methods to yield unit length oligomers. Cleavage can be performed as the multimers are formed or can be carried out after the reaction has terminated. Purification of the resultant oligomer can then be carried out if desired.

Under one embodiment, the restriction enzyme recognition site is designed into the ligation junction of the 3' terminal region and the 5' terminal region such that when these two terminal regions are ligated a restriction site is formed. After amplification, one can generate unit length monomers by cleaving the ligation junction with the restriction enzyme. This would also confirm that the reaction products visualized are the product of a successful ligation reaction as opposed to an artifact.

There are several techniques that can be used for the cleavage reaction. For example, restriction endonucleases can be used to cleave specific sequences that occur in the multimer. They can be used alone, or in some cases with the addition of a short DNA strand that aids in the reaction. The cleavage reaction can also be carried out using chemicals. For example, Maxam-Gilbert cleavage reagents can be used to cleave the strand at a base that occurs once between each oligomer.

For cleavage of RNA multimers, enzymatic or chemical techniques can be used. The enzyme Rnase H can be used along with the addition of a DNA oligomer, or base-specific Rnases can be used. Alternatively, a catalytic ribozyme can be used to cleave the multimer, or a self-cleaving sequence can be encoded into the multimer, which would cleave itself at the desired sites.

Another variation of the forward and reverse primers in CPA is to use a "uniprimer," which is a technique known for use in detecting PCR products. Nuovo et al., J. Histochem. Cytochem. 47(3):273-80 (1999), herein incorporated by reference. Neither the forward nor the reverse primer need contain a detectable label in such a system. Rather, one or both of the primers contains a "tail" which is the target for a third compound which contains a label, such as an energy transfer labeled hairpin primer to be stretched out in the next round of synthesis. Uniprimers are universal energy transfer-labeled primers used in combination with any target-specific primer pair. The target specific primers each have a 5' tail sequence, which is homologous to the 3' end of the uniprimer which, in turn, has a hairpin structure on the 5' end. The hairpin structure brings the fluorophore and quencher into close proximity when the primer is free in solution, providing efficient quenching. When the primer is incorporated into the amplification product, the hairpin structure is unfolded and a fluorescent signal can be detected.

Fluorescent moieties suitable for use in the present invention include, but are not limited to, Coumarin, fluorescein, 5-carboxyfluorescein (FAM), 2',7'-dimethoxy-4',5'-dichloro-6-carboxyfluorescein (JOE), rhodamine, 6-carboxy-X-rhodamine (ROX), N,N,N',N'-tetramethyl-6-carboxyrhodamine (TAMRA), 5-(2'-aminoethyl) aminonaphthalene-1-sulfonic acid (EDANS), Texan RED, fluorescent green protein and inorganic compounds. Quencher moieties suitable for use in the present invention include, but are not limited to, 4-(4'-dimethylaminophenylazo) benzoic acid (DABCYL), Acid Orange 12, Acid Orange 6, Acid Red 151, Mordant Black 17, Xylidyl Blue 17 and MANAMBSA. These fluorescent labels can be obtained from a number of commercial sources, including Sigma (St. Louis, Mo.), Molecular Probes (Eugene, Oreg.) and Research Organics (Cleveland, Ohio). It is understood that a person of skill in the art can mix and match various known fluorescers and quenchers based on their absorbance and emission spectrums to select optimal or appropriate pairs. Any label can be incorporated into the CPA complex by using a labeled dNTP or by hybridizing probe or antibody to DS-DNA that is labeled. Suitable labels include radioactive, fluorescent, chemiluminescent (e.g., luciferin, and luminol), enzymes (e.g., peroxidases, glucosidases, phosphatases, and esterases), ligands, cofactors, spin labels, magnetic, heavy metals, inorganic radical, chelating moiety, solid phases (e.g., latex beads, polystyrene beads, and metal sols) and indirect labels. Indirect labels are substances that directly or indirectly bind or interact with a labeled material such as biotin, digoxigenin, sequence tails, and haptens.

Pairs of interacting labels other than fluorescent and quenching moieties may also be used. Such pairs of interacting labels include, but are not limited to, enzyme or enzyme fragment and substrate, cofactor, coenzyme, inhibitor, activator or other modulator. Certain combinations of two enzymes may be used that interact differently when in close proximity, particularly with unstable compounds. Labeling and the selection of labels is well known to a person of skill in the art of nucleic acid binding assays, immunoassays, and ligand/receptor assays. Ligand/receptor assays include enzyme/substrate or inhibitor combinations, cell receptor/binding ligand, hormone receptors/hormones, etc. For purposes of illustration, one ligand/receptor assay is thyroxine binding to thyroxine receptor as an assay for thyroid function or cortisol/receptor.

In one embodiment of the present invention, a closed tube system is employed to enable detection of the amplicon without opening the reaction vessel, thereby minimizing the risk of contamination and facilitating automation of the present invention. Tyagi et al., Nature Biotech. 14:303-309 (1995), Holland et al., Proc. Natl. Acad. Sci. (USA) 88:7276-7280 (1991), Lee et al., Nucleic Acids Res. 21:3761-3766 (1993), all of which are herein incorporated by reference. The closed tube system can advantageously employ a molecular energy transfer mechanism.

Under one closed tube system of the present invention, all primers and all enzymes, including ligase, are added to the reaction tube as part of the reaction mixture. The reaction tube is then sealed and not reopened until after fluorescence emission is measured. Under this embodiment, a thermolabile ligase enzyme, such as T4 ligase, is often used. These ligase enzymes operate at temperatures ranging from about 4° C. to about 20° C. At these temperatures the polymerase enzymes used, Bst LF and thermostable polymerases are relatively, if not effectively, inactive. Alternatively, a thermostable ligase enzyme can be employed in the presence of one or more caged nucleotides. Kaplan et al., Biochem. 17(10):1929-

1935 (1978); McCray et al., Proc. Nat'l Acad. Sci. (USA) 77(12): 7237-7241 (1980), both of which are herein incorporated by reference. Caged nucleotides, which typically are 2-nitrobenzyl phosphate derivatives or 1-(2-nitro)phenylethyl phosphate derivatives, are unavailable to the DNA polymerase enzymes until after a fluorescent signal releases the nucleotide from the "cage."

The high specificity and potential for allele discrimination of padlock probes, along with their ability to be amplified by RCA-type methodology, is used by the present invention for solution-based single (or rare) target copy solid-phase diagnostic assays. RCA is generally considered to be inadequate for such applications because it is a linear amplification scheme.

Carefully designed padlock probes are capable of distinguishing single nucleotide changes in target nucleic acid samples. Methodologies for making such probes are known and capable of being designed by a person of ordinary skill in the art. To exploit the full potential of these probes, highly sensitive methods for their detection are also used. The analytical techniques used for solution-based assays involves geometrically amplifying the probe to extremely high levels by methods such as CRCA, PCR or CPA.

Most DNA ligases have the ability to discriminate mismatches with open circle probes. This ability, when combined with CPA has numerous uses, including genotyping, pharmogenetics, detecting specific point mutations, detecting polymorphisms, detecting rare events such as in cancer cells, allotyping, detecting genetic diseases, detecting aneuploidy, detecting microsatellite changes and detecting infectious microbes or nucleic acid containing compositions. The methods of the present invention may be used diagnostically on a variety of samples where the target nucleic acid (DNA or RNA) is either fixed on a solid phase or free in solution.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic *strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis*, Rickettsial pathogens, *Nocardia*, and *Acitnomycetes*.

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present invention include human immunodeficiency virus (HIV), human T-cell lymphocytotrophic virus, hepatitis viruses (e.g., Hepatitis B Virus (HBV) and Hepatitis C Virus (HCV)), Epstein-Barr Virus (EBV), cytomegalovirus (CMV), human papillomaviruses (HPV), human sarcomavirus (HSV), orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu, Bcr/Ab1, K-ras gene, RARA, c-myc and N-myc. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Some cancers and some genetic diseases are associated with base methylation. Esteller et al., New England J. Med. 343(19): 1350-1354 (2000), Herman et al., Proc. Nat'l Acad. Sci. (USA) 93: 9821-9826 (1996), Herman et al., Proc. Nat'l Acad. Sci. (USA) 91: 9700-9704 (1994), Merlo et al., Nat. Med. 1:686-692 (1995), Herman et al., Cancer Res. 56:722-727 (1996), Graff et al., Cancer Res. 55: 5195-5199 (1995), Lee et al., Cancer Epidemiology, Biomarkers & Prevention 6: 443-450 (1997), all of which are herein incorporated by reference. The present invention is capable of detecting these genetic mutations. Under this embodiment, the target nucleic acid molecule is treated with a chemical, such as sodium bisulfite, that converts all unmethylated cytosines to uracil. Primers capable of detecting these base changes are then used.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the agricultural industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Even organisms which cannot be cultured or are difficult to culture can be detected by the present invention. Furthermore, therapeutic agent sensitivities may be determined without a need to culture the organism. This is particularly useful for HIV, HCV, HPV, HSV, CMV, tuberculosis, leprosy, chlamydia, other difficult to culture microorganisms, and a wide range of eukaryotic and multicellular parasites. Some of these organisms may occur as only a single copy within or on a cell.

The following examples are provided by way of illustration and are not intended to be limiting of the present invention.

EXAMPLE I

Oligonucleotides and target DNAs: Padlock probes containing a 5' phosphate group were chemically synthesized by standard phosphoramidite chemistry and purified on denaturing polyacrylamide gels containing urea. The probe used for all of the examples was an 89mer (5'PO4-gcttgcacgaag-tactctggttctgactcgtcatgtct-cagctctagtacgctgatcttagtgtcaggatacggtaaatgaatcaaa gc -3'OH (SEQ ID NO.: 9)), with target arms directed against the cryptic plasmid of *Chlamydia trachomatis* serovar L1 (Hatt et al., Nucleic Acids Res. 16(9):4053-67 (1988), herein incorporated by reference) at positions 276-311. The ligation junction of the probe is located within the HinP1 restriction endonuclease site at position 296.

The target DNA for the *Chlamydia* studies was a PCR product (677 bp) generated from a plasmid vector containing the cryptic plasmid sequence of *Chlamydia trachomatis* serovar L1, with the probe ligation junction located 270 bases from the 5' end of the target DNA. The PCR product was prepared using a 20mer forward primer (5'-gtctttgcgcacagac-gatc-3' (SEQ ID NO.: 10)) and a 21mer reverse primer (5'-cgcccgcacgttctctcaagc-3' (SEQ ID NO.: 11)). Amplification was performed with a denaturation step (5 minutes at 95° C.) followed by 30 PCR cycles (30 seconds at 94° C.; 1 minute at 55° C.; 3 minutes at 72° C.) with a final extension step of 5 minutes at 72° C. The target DNA was quantitated against a Low DNA Mass Ladder (Gibco BRL) following gel electrophoresis in 1% agarose containing 0.5 µg/ml ethidium bromide, and verified by spectrophotometric measurement. PCR primers were removed by treatment with *E. coli* exonuclease I for 15 minutes at 37°, followed by incubation at 80° to inactivate the exonuclease.

The same 27mer forward primer was used for amplification of ligated padlock probes in the CRCA, PCR and CPA examples (5'-actagagctgagacatgacgagtcaga-3' (SEQ ID NO: 12)). All of the above primers were chemically synthesized with a 5'—OH and used without further purification except desalting. The reverse primer (36mer) used for amplification of ligated padlock probes in all examples was an energy transfer primer (5'F -atcagcaccctggctgat(d)cttagtgtcag-gatacgg-3' (SEQ ID NO: 13)) and was chemically synthesized to contain fluorescein (F) at the 5' end and DABSYL (D) at an internal T residue, and purified by HPLC. The underlined bases constitute the binding site of the primer.

Ligation reactions: Padlock probes were hybridized to denatured target DNA and circularized by treatment with a thermostable DNA ligase. 40 units of Taq™ DNA ligase (New England Biolabs) was added to a 30-□l reaction mixture containing 20 mM Tris-HCl (pH 7.6); 25 mM potassium acetate; 10 mM magnesium acetate; 1.0 mM NAD; 10 mM DTT (dithioltheitol), 0.1% Triton X-100; 100 nM padlock probe, and 500 nM *Chlamydia* target DNA. After an initial incubation at 95° C. for 2 minutes to denature the target DNA, ligation was performed during 8 cycles of denaturing at 95° for 1 minute and probe annealing and ligation at 50° C. for 4 minutes. Detection of ligated probe products was monitored by subjecting dilutions of the ligation reaction to CRCA, PCR, or CPA (see below). Control reactions were prepared as above except Taq™ DNA ligase was omitted.

Figure 3:
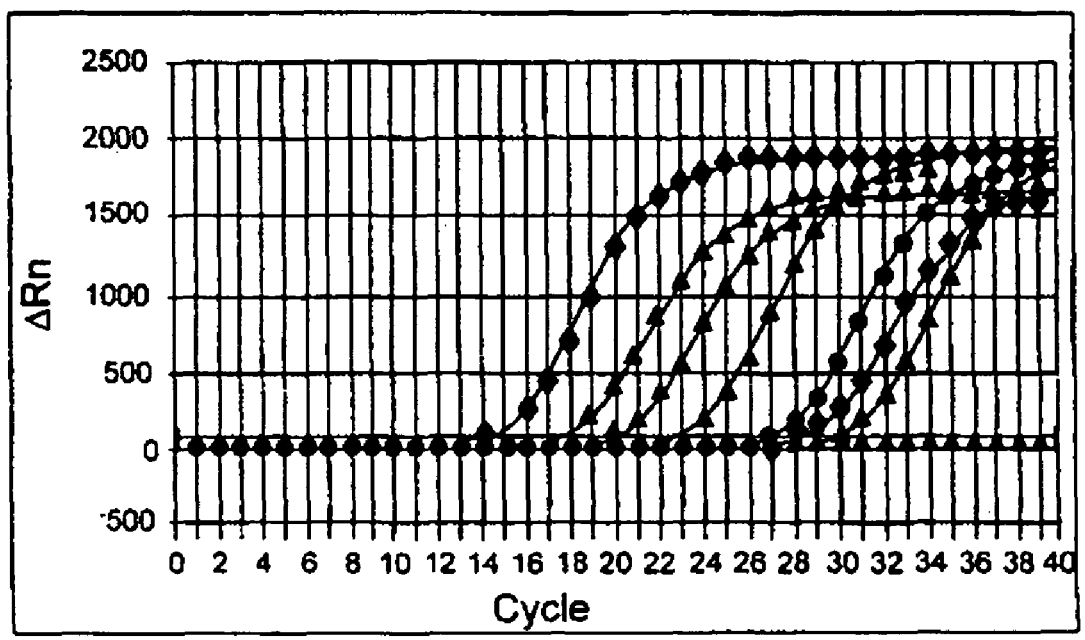
FIG. 3 provides an illustration of the change in fluorescent signal measured over time for a cascade rolling circle amplification of differing concentrations of a padlock probe.

Detection of padlock probes by CRCA: Aliquots (1 µl) of serial dilutions of ligation reactions were added to a reaction mixture (25 µl) containing 20 mM Tris-HCl (pH 8.8); 10 mM KCl; 10 mM $(NH_4)_2SO_4$; 2 mM $MgSO_4$, 0.1% Triton X-100; 200 mM dNTPs; 500 nM forward and reverse primers; and 4 units of Bst DNA polymerase (large fragment) (New England Biolabs). The serial dilutions yielded an estimated number of ligated probe molecules of $10^6$, $10^5$, $10^4$, $10^3$, $10^2$, $10^1$. Reactions were performed using a Prism™ 7700 Sequence Detection System to monitor the increase in fluorescence over time. During incubation at 63° C. for 50 2-minute intervals, the temperature was lowered to 50° C. for 15 seconds after each interval to monitor the increase in fluorescence as the reverse primer containing the fluorescein/DABSYL energy pair is incorporated into the CRCA product. FIG. 3 provides a schematic of the change in fluorescence over time measured for this reaction.

Detection of padlock probes by PCR: Aliquots (1 µl) of serial dilutions of ligation reactions were added directly to a PCR reaction mixture (25 µl) containing 20 mM Tris-HCl (pH 8.8); 10 mM KCl; 10 mM $(NH_4)_2SO_4$; 2 mM MgSO4, 0.1% Triton X-100; 200 µM dNTPs; 500 nM forward and reverse primers and either 2.5 units of Deep Vent™ polymerase (New England Biolabs) or 1.25 units of Platinum Taq™ polymerase (Life Technologies). The serial dilutions yielded an estimated number of ligated probe molecules of $10^6$, $10^5$, $10^4$, $10^3$, $10^2$, $10^1$. Following an initial heating step in the Prism™ 7700 (20 minutes at 63° C.), the DNA was denatured by heating to 94° for 2 minutes. This activates Platinum Taq™, while Deep Vent™ polymerase is already active. This was followed by 40 PCR cycles (15 seconds at 94° C.; 1 minute at 60° C.). Fluorescence was monitored during the 60° C. step. To examine the quality of the products, aliquots (2 µl) were analyzed on agarose gels as above. FIG. 4A and FIG. 5A provides a schematic of the change in fluorescence over time measured for the reaction with Deep Vent™ and Platinum Taq™, respectively.

Detection of padlock probes by CPA: The reaction conditions were identical to those described above for PCR, except that 4 units of Bst LF was included in the reaction mixture and the forward primer was modified to include nitroindole at positions 6 and 15. The Bst LF polymerase is inactivated following the initial incubation at 63° when the temperature is raised to 94° C., with Platinum Taq™ being simultaneously activated. Fluorescence was monitored and the products analyzed as above. FIG. 4B and FIG. 5B provides a schematic of the change in fluorescence over time measured for the reaction with Deep Vent™ and Platinum Taq™, respectively.

As shown by these results, CPA not only provides a detectable signal faster than either PCR or CRCA, but CPA also allows for the detection of minute quantities of nucleic acid molecules that are not detectable above background using PCR or CRCA.

EXAMPLE II

Oligonucleotides and target DNAs: The following padlock probes containing a 5' phosphate group were chemically synthesized by standard phosphoramidite chemistry and purified on denaturing polyacrylamide gels containing urea: 5'PO4-cctgcatgcactggatgcacttct-gactcgtcatgtctcagctctag-tacgctgatcttagtgtcaggatacggctggtgcaatagg c-3'OH, which is an 88mer directed against the gag gene of HIV (SEQ ID NO: 14);

5'PO4-cggttctgcttgtccagcttgc-gactcgtcatgtctgaactctag-tacgctgatcttagtgtcaggatacgggtaatgggctctgtc-3'OH (SEQ ID NO: 15), which is an 87mer directed against the E7 gene of HPV;

5'PO4-tcgtatgagtagaaggtgagttct-gactcgtcatgtctcagctctag-tacgctgatcttagtgtcaggatacggagttcatcagtt-3'OH (SEQ ID NO: 16), which is an 86mer directed against *Cryptosporidium parvum*;

5PO4-ccaaggagcagaggaggttctgactcgt-catgtctcagctctagtacgctgatct-tagtgtcaggatacggaggttaggtgaagga-3'OH (SEQ ID NO: 17), which is an 86mer directed against the Her-2/neu breast cancer gene;

5'PO4-ccaaccactcttctattctgactcgt-catgtctcagctctagtacgctgatct-tagtgtcaggatacggtactaaatcacaaca-3'OH (SEQ ID NO: 18), which is an 84mer designed to detect the unmethylated version of the GstPi gene (for monitoring methylation status in marker gene for prostate cancer); and 5'PO4-ccgaccgctcttctattctgactcgt-catgtctcagctctagtacgctgatct-tagtgtcaggatacggtactaaatcacgacg-3'OH (SEQ ID NO: 19), which is an 84mer designed to detect the methylated version of the GstPi gene (for monitoring methylation status in marker gene for prostate cancer).

The underlined sequences for each of the above-identified sequences reflect the target-complementary regions of the padlock probe molecule. The spacer region between the two target-complementary regions is the same for all of the padlock probe molecules with the exception of the HPV padlock probe molecule. That padlock probe molecule contains several changes in the spacer region that have been found to reduce background amplification.

All references, patents, and patent application cited herein are incorporated by reference in their entirety.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A nucleic acid amplification method comprising:
   (a) providing a closed circular padlock probe molecule; a target nucleic acid molecule; a forward primer; a reverse primer; dNTPs; and a first DNA polymerase to form a reaction mixture;
   (b) incubating said reaction mixture at about 50° C. to about 70° C. for 1 minute to 30 minutes;
   (c) creating a multi-tailed complex by cascade rolling circle amplification wherein the multi-tailed complex has multiple primer binding sites, and wherein the multi-tailed complex is not a detectable amplification product;
   (d) activating a second DNA polymerase, wherein said second DNA polymerase is thermostable; and
   (e) thermocycling said multi-tailed complex with said second DNA polymerase, wherein said thermocycling said multi-tailed complex generates a detectable amplification product.

2. The method of claim 1, wherein said first DNA polymerase is Bst LF.

3. The method of claim 1, wherein said second DNA polymerase is a polymerase enzyme derived from *Thermus aquaticus, Pyrococcus* species, *Thermococcus litoralis* or *Pyrococcus furiosus*.

4. The method of claim 1, wherein said second DNA polymerase is a recombinant thermostable polymerase.

5. The method of claim 4, wherein the recombinant thermostable polymerase is an antibody-inactivated polymerase or a chemically-inactivated polymerase.

6. The method of claim 1, wherein the reaction mixture further contains a strand displacement factor.

7. The method of claim 1, wherein said reaction mixture is incubated at about 50° C. to about 70° C. for about 3 minutes to about 20 minutes.

8. The method of claim 1, further comprising denaturing said first DNA polymerase.

9. The method of claim 1, wherein said target nucleic acid molecule is a single-stranded DNA molecule or a double-stranded DNA molecule.

10. The method of claim 1, wherein said target nucleic acid is a plasmid or fragment thereof, a genomic DNA or fragment thereof, a viral DNA or fragment thereof, a viral RNA or fragment thereof, an mRNA, a mitochondrial DNA or fragment thereof, or a chromosomal DNA or fragment thereof.

11. The method of claim 1, wherein at least one of said forward primer or reverse primer is detectably labeled.

12. The method of claim 11, wherein the detectably labeled primer contains a molecular energy transfer mechanism.

13. A method for detecting a target nucleic acid molecule in a sample comprising:
   (a) providing a target nucleic acid molecule, a linear padlock probe molecule, a ligase enzyme, a forward primer, a reverse primer, dNTPs, and a first DNA polymerase;
   (b) creating a closed circular padlock probe molecule:
   (c) incubating at about 50° C. to about 70° C. for 1 minute to 30 minutes;
   (d) creating a multi-tailed complex from said closed circular padlock probe molecule by cascade rolling circle amplification wherein the multi-tailed complex has multiple primer binding sites, and wherein the multi-tailed complex is not a detectable amplification product;
   (e) activating a second DNA polymerase;
   (f) thermocycling said multi-tailed complex with said second DNA polymerase wherein said thermocycling said multi-tailed complex generates a detectable amplification product; and
   (g) detecting the amplification product of said multi-tailed complex.

14. A method for detecting a target nucleic acid molecule in a sample comprising:
   (a) providing a target nucleic acid molecule, a closed circular padlock probe molecule topologically linked to said target nucleic acid molecule, a forward primer, a reverse primer, dNTPs, and a first DNA polymerase:
   (b) incubating at about 50° C. to about 70° C. for 1 minute to 30 minutes;
   (c) creating a multi-tailed complex from said closed circular padlock probe molecule by cascade rolling circle amplification wherein the multi-tailed complex has multiple primer binding sites, and wherein the multi-tailed complex is not a detectable amplification product;
   (d) activating a second DNA polymerase;
   (e) thermocycling said multi-tailed complex with said second DNA polymerase wherein said thermocycling said multi-tailed complex generates a detectable amplification product; and
   (f) detecting the amplification product of said multi-tailed complex.

15. A method for detecting a plurality of target nucleic acid molecules in a sample comprising:
   (a) providing a plurality of target nucleic acid molecules, a plurality of linear padlock probe molecules capable of annealing to a plurality of distinct target nucleic acid molecule, a ligase enzyme, dNTPs, and a first DNA polymerase;
   (b) creating at least two closed circular nucleic acid molecules, wherein each of said closed circular nucleic acid molecules is topologically linked to a distinct target nucleic acid molecule;
   (c) providing, for each member of said at least two closed circular nucleic acid molecules, a forward primer and a reverse primer;
   (d) incubating at about 50° C. to about 70° C. for 1 minute to 30 minutes;
   (e) creating a multi-tailed complex for each of said distinct target nucleic acid molecules by cascade rolling circle amplification wherein the multi-tailed complex has multiple primer binding sites, and wherein the multi-tailed complex is not a detectable amplification product;
   (f) activating a second DNA polymerase;
   (g) thermocycling said at least two distinct multi tailed complexes with said second DNA polymerase wherein said thermocycling said at least two distinct multi-tailed complexes generates detectable amplification products; and
   (h) detecting the amplification products of said at least two distinct multi-tailed complexes.

16. The method of claim 15, wherein said detection of the amplification products of the multi-tailed complexes is performed by a real-time detection instrument.

17. The method of claim 15, wherein said first DNA polymerase is Bst LF.

18. The method of claim 15, wherein said second DNA polymerase is a polymerase enzyme derived from *Thermus aquaticus, Pyrococcus* species, *Thermococcus litoralis* or *Pyrococcus furiosus*.

19. The method of claim 15, wherein said second DNA polymerase is a recombinant thermostable polymerase.

20. The method of claim 19, wherein the recombinant thermostable polymerase is an antibody-inactivated polymerase or a chemically-inactivated polymerase.

21. The method of claim 15, wherein the reaction mixture further contains a strand displacement factor.

22. The method of claim 15, wherein said incubating is at about 50° C. to about 70° C. for about 3 minutes to about 20 minutes.

23. The method of claim 15, further comprising denaturing said first DNA polymerase.

24. The method of claim 15, wherein, for at least one of said at least two closed circular nucleic acid molecules, at least one forward or reverse primer is labeled with a detectable label.

25. The method of claim 24, wherein the detectable label is a distinguishable detectable label.

26. A closed tube nucleic acid molecule amplification method comprising:
(a) providing a target nucleic acid molecule, a ligase enzyme; a forward primer; a reverse primer; dNTPs; and a first DNA polymerase in a reaction tube;
(b) sealing said reaction tube;
(c) creating a closed circular padlock probe molecule;
(d) incubating at about 50° C. to about 70° C. for 1 minute to 30 minutes;
(e) creating a multi-tailed complex from said closed circular padlock probe molecule by cascade rolling circle amplification wherein the multi-tailed complex has multiple primer binding sites, and wherein the multi-tailed complex is not a detectable amplification product;
(f) activating a second DNA polymerase, wherein said second DNA polymerase is a thermostable DNA polymerase; and
(g) thermocycling said multi-tailed complex with said second DNA polymerase, wherein said thermocycling said multi-tailed complex generates a detectable amplification product.

27. The method of claim 26, wherein the ligase enzyme is a thermolabile ligase enzyme.

28. The method of claim 26, wherein at least one dNTP is a caged dNTP.

29. The method of claim 1, wherein said target nucleic acid molecule is a single-stranded RNA molecule or a double-stranded RNA molecule.

30. The method of claim 1, wherein the 5' terminal region of said forward or reverse primer is a tailed primer molecule.

31. The method of claim 1, wherein at least one of the forward primer or reverse primer is a hairpin primer.

32. The method of claim 31, wherein the hairpin primer has a loop region that contains a restriction endonuclease cleavage site.

33. The method of claim 1, wherein at least one of said forward primer or reverse primer contains at least one non-informative base analog.

34. The method of claim 33, wherein said non-informative base analog is nitropyrrole or nitroindole.

35. The method of claim 1, wherein at least one of said forward primer or reverse primer contains at least one polarity switch.

36. The method of claim 15, wherein, for at least one of said at least two closed circular nucleic acid molecules, the 5' terminal region of said forward primer or reverse primer does not hybridize to the closed circular nucleic acid molecule.

37. The method of claim 15, wherein, for at least one of said at least two closed circular nucleic acid molecules, at least one of said forward primer or reverse primer is a hairpin primer.

38. The method of claim 37, wherein the hairpin primer has a loop region that contains a restriction endonuclease cleavage site.

39. The method of claim 15, wherein, for at least one of said at least two closed circular nucleic acid molecules, at least one of said forward primer or reverse primer contains at least one non-informative base analog.

40. The method of claim 39, wherein said modified non-informative base analog is nitropyrrole or nitroindole.

41. The method of claim 15, wherein, for at least one of said at least two closed circular nucleic acid molecules, at least one of said forward primer or reverse primer contains at least one polarity switch.

* * * * *

SEQUENCE LISTING

<160> NUMBER OF SEQ ID NOS: 20

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
actagagctg agaca                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
actagagttc agaca                                                      15

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 3
actagagctg agacatgacg a                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actagagttc agacatgacg a                                             21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actagagctg agacatgacg agtc                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actagagttc agacatgacg agtc                                          24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actagagctg agacatgacg agtcgca                                       27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actagagttc agacatgacg agtcgca                                       27

<210> SEQ ID NO 9
<211> LENGTH: 89
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 9
gcttgcacga agtactctgg ttctgactcg tcatgtctca gctctagtac gctgatctta     60
gtgtcaggat acggtaaatg aatcaaagc                                       89

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtctttgcgc acagacgatc                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcccgcacg ttctctcaag c                                               21

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actagagctg agacatgacg agtcaga                                         27

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcagcaccc tggctgatct tagtgtcagg atacgg                               36

<210> SEQ ID NO 14
<211> LENGTH: 88
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cctgcatgca ctggatgcac ttctgactcg tcatgtctca gctctagtac gctgatctta     60
gtgtcaggat acggctggtg caataggc                                        88

<210> SEQ ID NO 15
<211> LENGTH: 87
<212> TYPE: DNA
<213> ORGANISM: Artificial Sequence
<220> FEATURE:
<223> OTHER INFORMATION: Description of Artificial Sequence: Synthetic

```
probe

<400> SEQUENCE: 15
cggttctgct tgtccagctt gcgactcgtc atgtctgaac tctagtacgc tgatcttagt      60
gtcaggatac gggtaatggg ctctgtc                                          87

<210> SEQ ID NO 16
<211> LENGTH: 86
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tcgtatgagt agaaggtgag ttctgactcg tcatgtctca gctctagtac gctgatctta      60
gtgtcaggat acggagttca tcagtt                                           86

<210> SEQ ID NO 17
<211> LENGTH: 86
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ccaaggagca gaggaggttc tgactcgtca tgtctcagct ctagtacgct gatcttagtg      60
tcaggatacg gaggttaggt gaagga                                           86

<210> SEQ ID NO 18
<211> LENGTH: 84
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ccaaccactc ttctattctg actcgtcatg tctcagctct agtacgctga tcttagtgtc      60
aggatacggt actaaatcac aaca                                             84

<210> SEQ ID NO 19
<211> LENGTH: 84
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ccgaccgctc ttctattctg actcgtcatg tctcagctct agtacgctga tcttagtgtc      60
aggatacggt actaaatcac gacg                                             84

<210> SEQ ID NO 20
<211> LENGTH: 124
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ccagagtact tcgtgcaagc cgaaactaag taaatggcat aggactgtga ttctagtcgc      60
```

```
atgatctcga ctctgtactg ctcagtcttg gtctcatgaa gcacgttcgg ctttgattca    120
ttta                                                                 124
```